United States Patent
Vonwiller et al.

(10) Patent No.: US 8,016,832 B2
(45) Date of Patent: Sep. 13, 2011

(54) INSTALLATION SYSTEMS FOR SPINAL STABILIZATION SYSTEM AND RELATED METHODS

(75) Inventors: Stephan Vonwiller, Wintherthur (CH); Mark W. Darst Rice, Minneapolis, MN (US)

(73) Assignee: Zimmer Spine, Inc., Minneapolis, MN (US)

(*) Notice: Subject to any disclaimer, the term of this patent is extended or adjusted under 35 U.S.C. 154(b) by 618 days.

(21) Appl. No.: 11/743,481

(22) Filed: May 2, 2007

(65) Prior Publication Data
US 2008/0275456 A1 Nov. 6, 2008

(51) Int. Cl.
*A61B 17/70* (2006.01)
(52) U.S. Cl. .......... 606/86 A; 606/99; 606/914
(58) Field of Classification Search .......... 606/60, 606/246, 250–279, 99, 104, 914, 86 A
See application file for complete search history.

(56) References Cited

U.S. PATENT DOCUMENTS

| | | | |
|---|---|---|---|
| 4,960,420 A * | 10/1990 | Goble et al. | 606/232 |
| 5,030,220 A | 7/1991 | Howland | |
| 5,540,688 A | 7/1996 | Navas | |
| 5,562,660 A | 10/1996 | Grob | |
| 5,584,831 A | 12/1996 | McKay | |
| 5,885,299 A * | 3/1999 | Winslow et al. | 606/99 |
| 5,941,885 A | 8/1999 | Jackson | |
| 6,139,549 A * | 10/2000 | Keller | 606/86 A |
| 6,224,598 B1 | 5/2001 | Jackson | |
| 6,235,028 B1 * | 5/2001 | Brumfield et al. | 606/53 |
| 6,290,700 B1 | 9/2001 | Schmotzer | |
| 6,440,132 B1 | 8/2002 | Jackson | |
| 6,440,136 B1 | 8/2002 | Gambale et al. | |
| 6,458,132 B2 | 10/2002 | Choi | |
| 6,530,929 B1 | 3/2003 | Justis et al. | |
| 6,540,749 B2 | 4/2003 | Schafer et al. | |
| 6,565,565 B1 | 5/2003 | Yuan et al. | |
| 6,585,737 B1 | 7/2003 | Baccelli et al. | |
| 6,652,526 B1 | 11/2003 | Arafiles | |
| 6,660,005 B2 | 12/2003 | Toyama et al. | |
| 6,726,687 B2 | 4/2004 | Jackson | |
| 6,730,089 B2 | 5/2004 | Jackson | |
| 6,730,093 B2 | 5/2004 | Saint Martin | |
| 6,790,209 B2 * | 9/2004 | Beale et al. | 606/86 A |
| 6,884,244 B1 | 4/2005 | Jackson | |
| 6,932,822 B2 | 8/2005 | Oribe et al. | |

(Continued)

FOREIGN PATENT DOCUMENTS

EP 0-669-109 B1 8/1995

(Continued)

*Primary Examiner* — Eduardo C Robert
*Assistant Examiner* — Jerry Cumberledge
(74) *Attorney, Agent, or Firm* — Seager Tufte & Wickhem LLC

(57) ABSTRACT

A system for implantation of a spinal stabilization system includes a vertebral anchor having a top portion. The top portion has a perimeter and a first engaging element. The first engaging element has a first longitudinal axis that is generally parallel to a second longitudinal axis of the top portion. The perimeter extends around the second longitudinal axis. The system also includes a driving tool that has a second engaging element that is configured to cooperate with the first engaging element to substantially restrict rotation of the driving tool relative to the top portion about the second longitudinal axis. The first engaging element is configured to slidably receive the second engaging element in a direction along the first longitudinal axis, and the second engaging element is configured to extend substantially within the perimeter of the top portion.

26 Claims, 17 Drawing Sheets

U.S. PATENT DOCUMENTS

| | | | |
|---|---|---|---|
| 6,986,771 B2 | 1/2006 | Paul et al. | |
| 6,989,011 B2 | 1/2006 | Paul et al. | |
| 6,994,710 B2 | 2/2006 | White et al. | |
| 6,997,927 B2 | 2/2006 | Jackson | |
| 7,018,378 B2 | 3/2006 | Biedermann et al. | |
| 7,090,679 B2 | 8/2006 | Saint-Martin et al. | |
| 7,156,850 B2 | 1/2007 | Kim | |
| 7,160,300 B2 | 1/2007 | Jackson | |
| 7,179,261 B2 | 2/2007 | Sicvol et al. | |
| 7,223,268 B2 | 5/2007 | Biedermann | |
| 7,326,210 B2 | 2/2008 | Jahng et al. | |
| 7,422,597 B1* | 9/2008 | Alby | 606/246 |
| 2002/0035366 A1 | 3/2002 | Walder et al. | |
| 2002/0133154 A1 | 9/2002 | Saint Martin | |
| 2002/0133159 A1 | 9/2002 | Jackson | |
| 2003/0045900 A1* | 3/2003 | Hahnen et al. | 606/205 |
| 2003/0050645 A1* | 3/2003 | Parker et al. | 606/99 |
| 2004/0087958 A1* | 5/2004 | Myers et al. | 606/80 |
| 2004/0138662 A1 | 7/2004 | Landry et al. | |
| 2004/0143265 A1 | 7/2004 | Landry et al. | |
| 2004/0172022 A1 | 9/2004 | Landry et al. | |
| 2004/0181224 A1 | 9/2004 | Biedermann et al. | |
| 2004/0186478 A1 | 9/2004 | Jackson | |
| 2004/0243193 A1 | 12/2004 | Ballis | |
| 2005/0038432 A1* | 2/2005 | Shaolian et al. | 606/61 |
| 2005/0065516 A1 | 3/2005 | Jahng | |
| 2005/0085815 A1 | 4/2005 | Harms et al. | |
| 2005/0124991 A1 | 6/2005 | Jahng | |
| 2005/0131408 A1 | 6/2005 | Sicvol et al. | |
| 2005/0131422 A1 | 6/2005 | Anderson et al. | |
| 2005/0143737 A1 | 6/2005 | Pafford et al. | |
| 2005/0149053 A1 | 7/2005 | Varieur et al. | |
| 2005/0154390 A1 | 7/2005 | Biedermann et al. | |
| 2005/0192579 A1 | 9/2005 | Jackson | |
| 2005/0203513 A1 | 9/2005 | Jahng et al. | |
| 2005/0203514 A1 | 9/2005 | Jahng et al. | |
| 2005/0203517 A1 | 9/2005 | Jahng et al. | |
| 2005/0228395 A1* | 10/2005 | Auxepaules et al. | 606/91 |
| 2005/0234451 A1 | 10/2005 | Markworth | |
| 2005/0245928 A1* | 11/2005 | Colleran et al. | 606/61 |
| 2005/0277925 A1 | 12/2005 | Mujwid | |
| 2006/0025768 A1 | 2/2006 | Iott et al. | |
| 2006/0064090 A1 | 3/2006 | Park | |
| 2006/0069390 A1 | 3/2006 | Frigg et al. | |
| 2006/0074418 A1 | 4/2006 | Jackson | |
| 2006/0079894 A1 | 4/2006 | Colleran et al. | |
| 2006/0079903 A1 | 4/2006 | Wong | |
| 2006/0079909 A1* | 4/2006 | Runco et al. | 606/99 |
| 2006/0084993 A1 | 4/2006 | Landry et al. | |
| 2006/0089644 A1 | 4/2006 | Felix | |
| 2006/0095038 A1 | 5/2006 | Jackson | |
| 2006/0100621 A1 | 5/2006 | Jackson | |
| 2006/0100622 A1 | 5/2006 | Jackson | |
| 2006/0106380 A1 | 5/2006 | Colleran et al. | |
| 2006/0111712 A1 | 5/2006 | Jackson | |
| 2006/0111713 A1 | 5/2006 | Jackson | |
| 2006/0111715 A1 | 5/2006 | Jackson | |
| 2006/0122597 A1 | 6/2006 | Jones et al. | |
| 2006/0122602 A1 | 6/2006 | Konieczynski et al. | |
| 2006/0142758 A1 | 6/2006 | Petit | |
| 2006/0142761 A1 | 6/2006 | Landry et al. | |
| 2006/0149237 A1 | 7/2006 | Markworth et al. | |
| 2006/0173454 A1 | 8/2006 | Spitler et al. | |
| 2006/0195086 A1 | 8/2006 | Sybert | |
| 2006/0195093 A1 | 8/2006 | Jahng | |
| 2006/0195095 A1 | 8/2006 | Mueller et al. | |
| 2006/0200128 A1 | 9/2006 | Mueller | |
| 2006/0200129 A1 | 9/2006 | Denti | |
| 2006/0200132 A1 | 9/2006 | Chao et al. | |
| 2006/0200133 A1 | 9/2006 | Jackson | |
| 2006/0200136 A1 | 9/2006 | Jackson | |
| 2006/0212033 A1 | 9/2006 | Rothman et al. | |
| 2006/0247630 A1* | 11/2006 | Iott et al. | 606/61 |
| 2006/0247645 A1* | 11/2006 | Wilcox et al. | 606/86 |
| 2007/0016200 A1 | 1/2007 | Jackson | |
| 2007/0055244 A1 | 3/2007 | Jackson | |
| 2007/0078460 A1* | 4/2007 | Frigg et al. | 606/61 |
| 2007/0129729 A1 | 6/2007 | Petit et al. | |
| 2007/0198088 A1 | 8/2007 | Biedermann et al. | |
| 2007/0227314 A1* | 10/2007 | Erickson et al. | 81/467 |
| 2007/0270860 A1 | 11/2007 | Jackson | |
| 2007/0293862 A1 | 12/2007 | Jackson | |
| 2007/0293869 A1* | 12/2007 | Conte et al. | 606/91 |
| 2008/0091213 A1 | 4/2008 | Jackson | |
| 2008/0140076 A1 | 6/2008 | Jackson | |
| 2008/0147122 A1 | 6/2008 | Jackson | |
| 2008/0161857 A1 | 7/2008 | Hestad et al. | |
| 2008/0177317 A1 | 7/2008 | Jackson | |
| 2008/0183216 A1 | 7/2008 | Jackson | |
| 2009/0005817 A1 | 1/2009 | Friedrich et al. | |

FOREIGN PATENT DOCUMENTS

| | | | |
|---|---|---|---|
| EP | 0669109 A1 | 8/1995 | |
| EP | 0669109 B1 | 5/1999 | |
| EP | 1523949 A1 | 4/2005 | |
| EP | 1523949 B1 | 6/2007 | |
| FR | 2715057 A1 | 7/1995 | |
| FR | 2844180 A1 | 3/2004 | |
| FR | 2867057 A1 | 9/2005 | |
| NL | 7610576 | 3/1978 | |
| WO | 9417745 A1 | 8/1994 | |
| WO | 9519149 A1 | 7/1995 | |
| WO | WO 98/41159 | * | 9/1998 |
| WO | 9905980 A1 | 2/1999 | |
| WO | 2004-041100 | 10/2003 | |
| WO | 2004-004549 A2 | 1/2004 | |
| WO | 2004024011 A1 | 3/2004 | |
| WO | 2005087121 A1 | 9/2005 | |
| WO | 2006066685 A1 | 6/2006 | |
| WO | 2008134703 A2 | 11/2008 | |

* cited by examiner

INSTALLATION SYSTEMS FOR SPINAL STABILIZATION SYSTEM AND RELATED METHODS

FIELD OF THE INVENTION

This invention relates generally to spinal fixation surgery and, more specifically, to systems enabling installation of anchors of spinal stabilization constructs.

BACKGROUND

The spinal column is a highly complex system of bones and connective tissues that provides support for the body and protects the delicate spinal flexible connecting member and nerves. The spinal column includes a series of vertebrae stacked one on top of the other, each vertebral body including an inner or central portion of relatively weak cancellous bone and an outer portion of relatively strong cortical bone. An intervertebral disc is situated between each vertebral body to cushion and dampen compressive forces experienced by the spinal column. A vertebral canal containing the spinal cord and nerves is located posterior to the vertebral bodies. In spite of the complexities, the spine is a highly flexible structure, capable of a high degree of curvature and twist in nearly every direction. For example, the kinematics of the spine normally includes flexion, extension, rotation and lateral bending.

There are many types of spinal column disorders including scoliosis (abnormal lateral curvature of the spine), kyphosis (abnormal forward curvature of the spine, usually in the thoracic spine), excess lordosis (abnormal backward curvature of the spine, usually in the lumbar spine), spondylolisthesis (forward displacement of one vertebra over another, usually in a lumbar or cervical spine) and other disorders caused by abnormalities, disease, or trauma, such as ruptured or slipped discs, degenerative disc disease, fractured vertebra, and the like. Patients that suffer from such conditions usually experience extreme and debilitating pain as well as diminished range of motion and nerve function. These spinal disorders may also threaten the critical elements of the nervous system housed within the spinal column.

One particular spinal fixation technique includes immobilizing portions of the spine of a patient by using connecting elements such as relatively rigid orthopedic spine rods that run generally parallel to the spine. Another technique utilizes less rigid connecting elements to provide a more dynamic stabilization of the affected regions of the spine. One example of such a spinal stabilization system is offered by the assignee of this invention, Zimmer Spine, Inc., as Dynesys® and is disclosed in European Patent No. 669,109, which is hereby incorporated by reference entirely. As used herein, the terms "spinal stabilization system", "spinal stabilization construct" and similar terms encompass any type of connecting element extending between adjacent vertebrae regardless of its rigidity, flexibility or construction. Installation of such systems may be accomplished, for example, by exposing the spine posteriorly and fastening hooks, bone screws, or anchors to the pedicles of the appropriate vertebrae. The vertebral anchors may be generally placed in a quantity of two per vertebrae, one at each pedicle on either side of the spine and serve as anchor points for the connecting elements.

Installation of such spinal stabilization constructs with vertebral anchors may thus require a surgeon to prepare an incision aligned with the spine of a patient. The vertebral anchors may then be attached to a number of vertebrae after which the connecting element is located with respect to receiving portions of the vertebral anchors. Fastening of a vertebral anchor may involve inserting a tool through the incision to engage the anchor such that actuation of the tool causes the anchor to engage the pedicle or other suitably chosen part of the vertebra. For example, a top portion of a threaded pedicle screw can be engaged by a tool such that rotation thereof in turn rotates the pedicle screw. Rotation of the pedicle screw then threadably engages the vertebra thereby securely mounting the anchor.

Known installation systems and techniques for spinal stabilization systems may be such that an interface between an instrument and an anchor allows some level of loose rotational and/or axial engagement or "play" between them, which may be undesirable to some users. Some systems also include multiple instruments to allow for engagement and rotation of the anchors and do not allow for top loading of elements of the stabilization system into the anchors. Therefore, systems and related methods to provide installation of a spinal stabilization construct and which address some of the drawbacks of known systems are highly desirable.

SUMMARY OF THE INVENTION

This invention addresses these and other shortcomings in the prior art. The devices and methods associated with this invention are used to aid in the surgery and installation of spinal stabilization systems and associated components, particularly the vertebral anchors of a spinal stabilization system.

In one embodiment, a system for implantation of a spinal stabilization system includes an anchor, such as a pedicle screw, which in turn includes a top portion. The top portion has a perimeter and a first engaging element. The first engaging element has a first longitudinal axis that is generally parallel to a second longitudinal axis of the top portion. The perimeter extends around the second longitudinal axis.

The system also includes a driving tool that has a second engaging element that is configured to cooperate with the first engaging element to substantially restrict rotation of the driving tool relative to the top portion about the second longitudinal axis.

In specific aspects of this embodiment, the first engaging element is configured to slidably receive the second engaging element in a direction along the first longitudinal axis, and the second engaging element is configured to extend substantially within the perimeter of the top portion.

In a specific embodiment, the first engaging element is further configured as a female element such as one having a generally trapezoidal shape. In another specific embodiment, the second engaging element is further configured as a male element such as one having a generally trapezoidal shape.

In one embodiment, the second engaging element includes an outwardly extending member; and the first engaging element includes a recess configured to receive at least a portion of the outwardly extending member to thereby axially retain the second engaging element therein. The outwardly extending member may be further configured as an outwardly biasing member.

In another embodiment, the driving tool includes an outer shield adapted to restrict radially outward movement of the second engaging element. The driving tool may also include a slot adapted to guide a connecting member of the spinal stabilization system toward the top portion of the anchor.

In another embodiment, the driving tool includes a securing member configured to secure a connecting element of the spinal stabilization system against the top portion of the anchor. In one aspect of this embodiment, the driving tool may further include a guide wire, such that the securing member is releasably coupled to the guide wire and such that the securing member is further configured to be coupled to the top portion of the anchor.

In a specific embodiment, the second engaging element extends fully within the perimeter of the top portion. In another specific embodiment, the second engaging element further includes a tapered end adapted to facilitate engagement thereof with the first engaging element. In yet another specific embodiment, the top portion may include a generally U-shaped channel configured to receive a connecting element of the spinal stabilization system therein.

The invention also includes various methods to install the vertebral anchor utilizing the driving tool and the associated advantages and features not found in the prior art.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein.

DETAILED DESCRIPTION OF THE INVENTION

Figure 1:
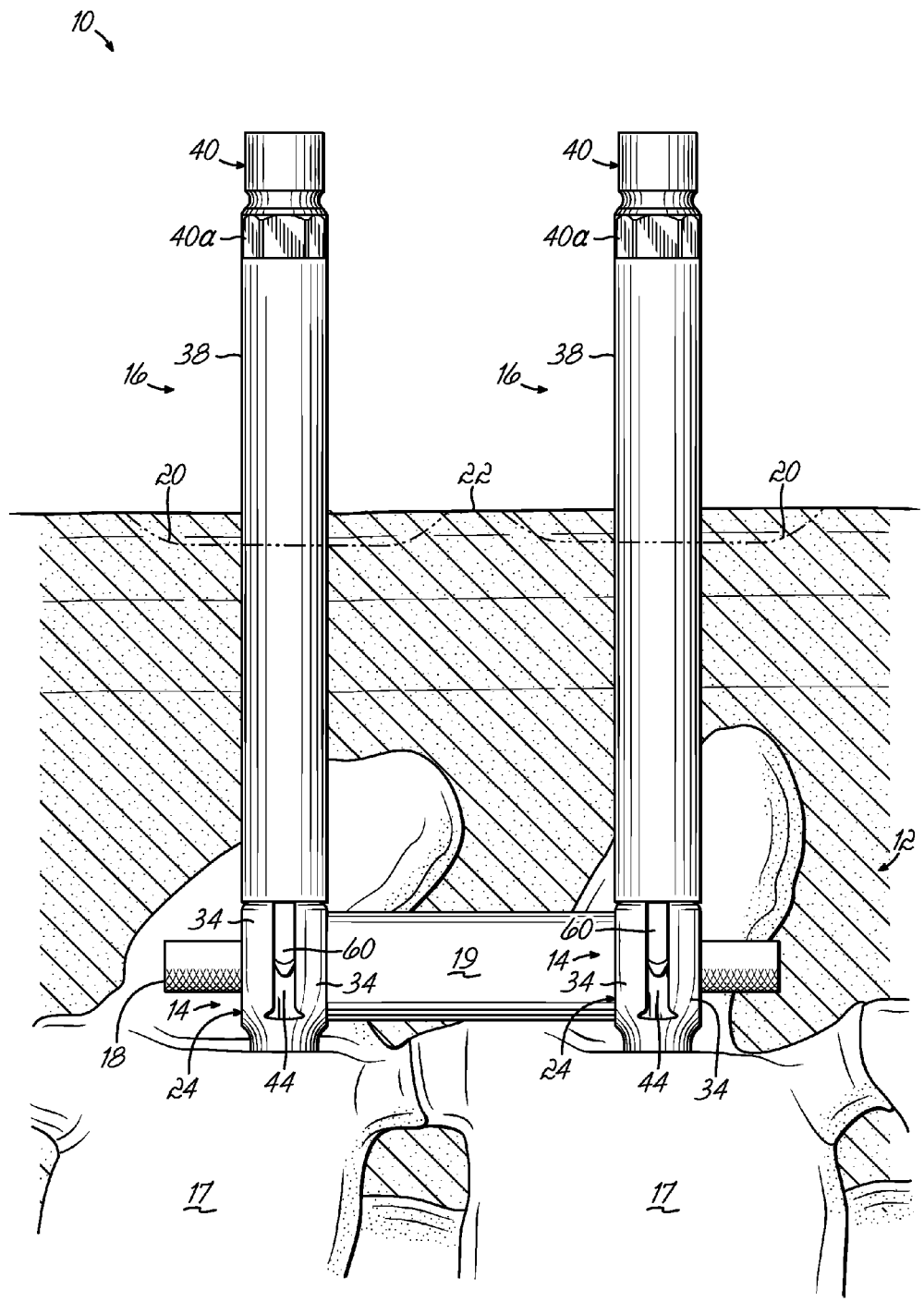
FIG. 1 is an elevational view of a spinal stabilization construct and installation system in accordance with one embodiment of the invention.

Referring to the drawings, and more particularly to FIG. 1, an installation system 10 according to one embodiment is shown for implantation of an exemplary spinal stabilization system or construct 12. The spinal stabilization system 12 includes a number of vertebral anchors 14 such as pedicle screws in one embodiment and the top loading installation system 10 includes a driving tool or instrument 16 that engages and drives each of the anchors 14 into selected vertebrae 17 of a patient. The installation system 10 thus permits implantation of the spinal stabilization construct 12 that, in one aspect, includes a connecting element 18 such as one in the form of a rigid rod or a more flexible construct of a cord and flexible member 19 (see FIG. 1) as in the Dynesys® system offered by Zimmer Spine, Inc., the assignee of this invention, to control relative motion of adjacent vertebrae 17. In one embodiment, the flexible member 19 may be formed from polycarbonate urethane and the connecting element 18 is a cord that may be formed from polyethylene-terephthalate, although it will be recognized that various other materials suitable for implantation within the human body and for providing stabilization of the spine while maintaining flexibility may be used. In other embodiments, the connecting element 18 and flexible member 19 can be constructed of other flexible materials such as metal, polymeric materials, or combinations of flexible materials.

Implantation of the spinal stabilization construct 12 may further involve, for example, inserting the instrument through an incision 20 through the skin 22 of the patient, in a region proximate the vertebrae 17. The incision may be sized for minimally invasive percutaneous or retractor based techniques or may be used in open procedures.

Figure 2:
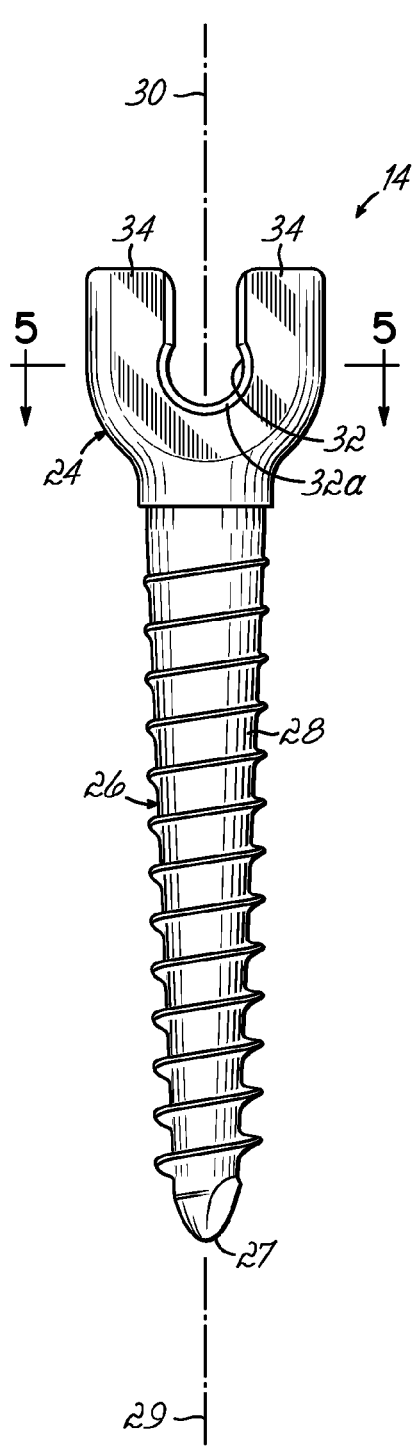
FIG. 2 is an elevational view of a vertebral anchor of a spinal fixation installation system in accordance with one embodiment of this invention.

With reference to FIGS. 1-3, the installation system 10 in this embodiment includes, as described above, a vertebral anchor 14 such as one in the form of a pedicle screw and an instrument 16 that cooperates with a top portion 24 of the vertebral anchor 14 to engage the vertebral anchor 14 for subsequent implantation into the vertebra 17. Accordingly, the installation system includes an interface between the vertebral anchor 14 and the instrument 16 to facilitate a suitable engagement there between.

With particular reference to FIG. 2, the vertebral anchor 14 includes, in addition to the top portion 24 thereof, a shank 26 connected to or integrally formed with the top portion 24. The shank 26 is suitably designed to engage the vertebrae 17. To this end, the shank 26 may include a tapered distal end 27 and a threaded surface 28 such that rotation, such as clockwise rotation of the shank 26, causes the vertebral anchor 14 to advance into the vertebra 17 generally in a direction of a longitudinal axis 29 of the shank 26 which may further be coaxial (though not necessarily) with an axis 30 of the top portion 24. Persons of ordinary skill in the art will appreciate that, alternatively, the threaded surface 28 may be designed such that counter-clockwise rotation of the shank 26 causes the vertebral anchor 14 to advance into the vertebra 17.

While the embodiment of FIG. 2 depicts a vertebral anchor 14 in the form of an exemplary pedicle screw that is uniaxial and which further has a top portion 24 as shown, it is contemplated that, alternatively, the anchor could be of a different type and/or include a top portion that differs from that shown in FIG. 2. For example, and without limitation, the vertebral anchor may be one in the form of a polyaxial screw (not shown) such that the top portion thereof differs from the top portion 26 of FIG. 2 in that it has an axis that is not necessarily coaxial or parallel with an axis of the shank of the polyaxial screw. The vertebral anchor may also include a hole or cannulation through its center to accommodate a K-wire that may be used in a minimally invasive procedure.

With continued reference to FIG. 2, the exemplary vertebral anchor 14 includes, as described above, a top portion 24. In the shown exemplary embodiment, the top portion is generally U-shaped and includes a channel 32 configured to receive the connecting element 18. More specifically, and with particular reference to the orientation depicted in FIG. 2, the channel is configured such that the connecting element 18 lies with a reference axis thereof (not shown) extending in a direction into a plane of the drawing i.e., generally perpendicular to the longitudinal axis 30 of the top portion 24. In one aspect of the shown embodiment, the channel may include tapered edges 32a to facilitate receipt therein of the connecting element 18. The top portion 24 of the vertebral anchor 14 shown in FIG. 1 is generally referred to as a top loading vertebral anchor in that the connecting element 18 is coupled to the top portion 24 generally from the top direction.

Figure 5:
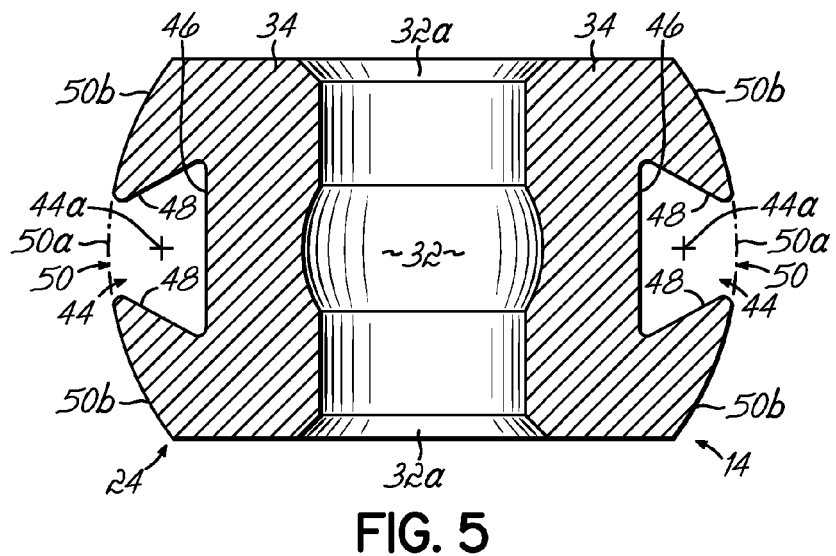
FIG. 5 is a cross-sectional view taken along line 5-5 of FIG. 2.
Figure 6:
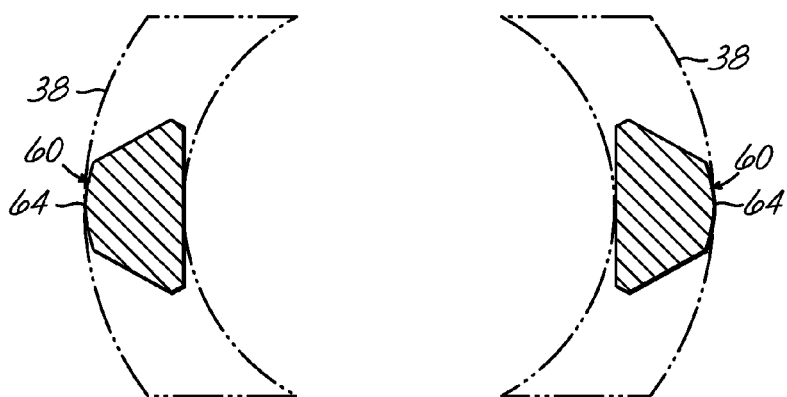
FIG. 6 is a cross-sectional view taken along line 6-6 of FIG. 3A.

The top portion 24 of the vertebral anchor 14 may further include a threaded region 33 (FIG. 5) disposed on walls 34 and configured to receive a securing member such as one in the form of a set screw (not shown) which in turn secures the connecting element against surfaces defining the channel, thereby securing the connecting element 18 in position relative to the vertebra 17 (FIG. 1).

While the exemplary embodiment of FIG. 2 depicts a vertebral anchor 14 in the form of a pedicle screw which is further uniaxial, includes a generally U-shaped top portion 24 and a tapered distal end 27, those of ordinary skill in the art will readily appreciate that any suitably chosen vertebral anchor of any other type, shape and/or relative dimensions may substitute the exemplary vertebral anchor 14 of FIG. 2. Similarly, while the exemplary vertebral anchor 14 of FIG. 2 is described as being configured to receive a connecting element in any form such as, and without limitation, a rigid rod, a semi-rigid construct or a flexible construct.

Figure 3A:
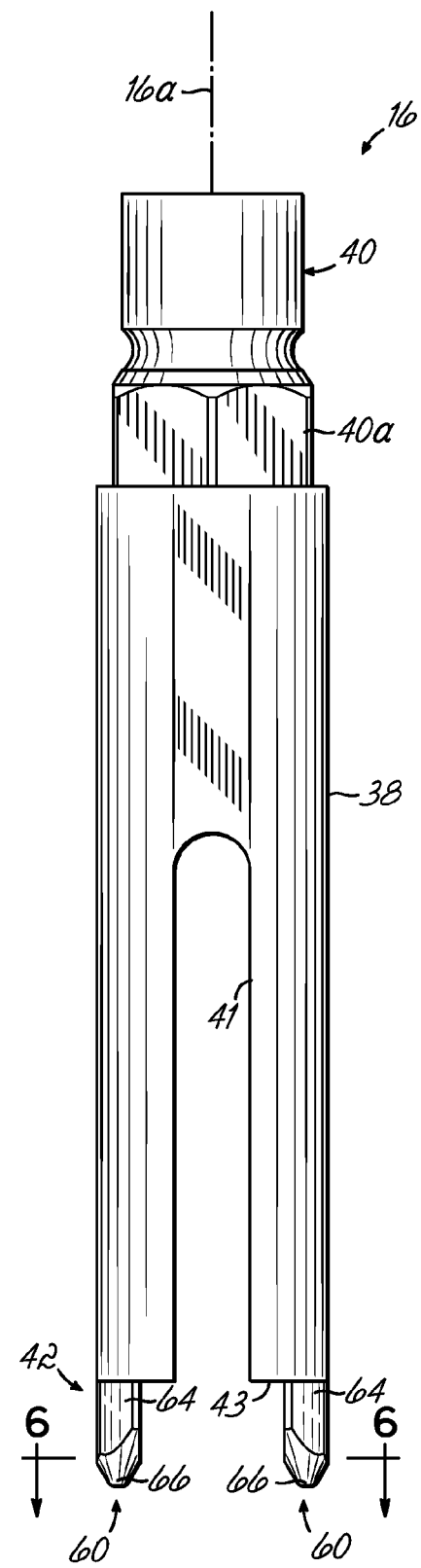
FIG. 3A is an elevational view of an embodiment of an instrument for implantation of the vertebral anchor of FIG. 2.
Figure 3B:
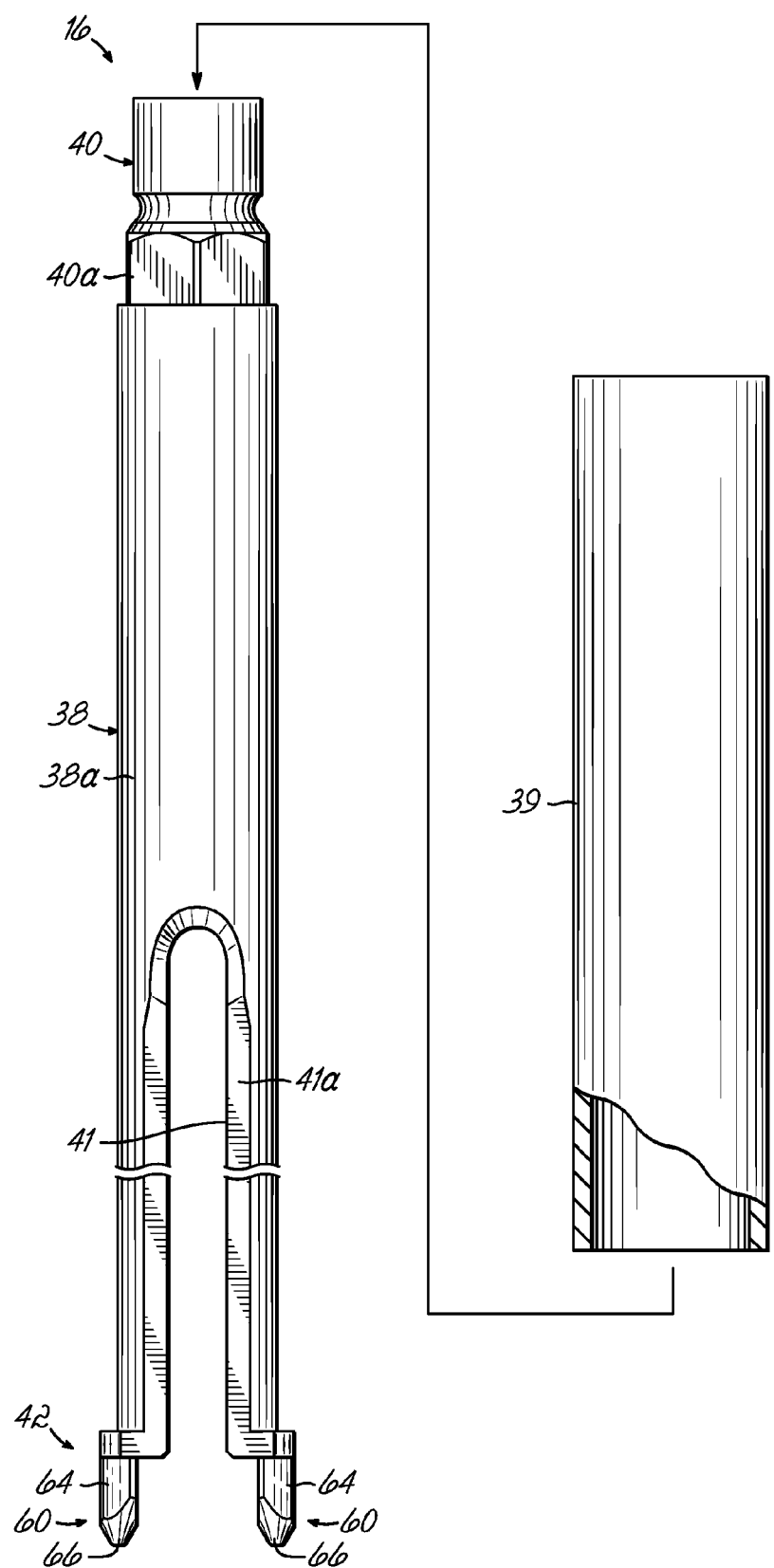
FIG. 3B is an elevational view of another embodiment of an instrument for implantation of the vertebral anchor of FIG. 2.

With reference to FIGS. 3A and 3B, the instrument 16 in these embodiments include a generally elongate body 38 and an actuator in the form, for example and without limitation, of a gripping portion 40. The gripping portion 40 includes a polygonal portion 47. The elongate body 38 may be made of one or more rigid materials such as a biocompatible metal and have a length suitably chosen to facilitate engagement of the instrument 16 with the vertebral anchor 14 and further to provide a surgeon with sufficient room to actuate the instrument. For example, and without limitation, the elongate body 38 may have a length such that the surgeon may percutaneously grip the gripping portion 40 with a suitable tool and rotate the instrument to cause corresponding rotation of the vertebral anchor. In one aspect of this shown embodiment, the exemplary gripping portion 40 is in the form of a polygonal structure (only 3 sides thereof shown in FIGS. 3A and 3B) such as a hexagonal structure. Accordingly, actuation of the instrument 16 may include coupling or engaging the gripping portion 40 with a hexagonal wrench, driver or tool (not shown) and manually rotating the wrench to cause a corresponding rotation of the instrument 16 which, in turn, rotates the vertebral anchor.

In one aspect of the exemplary embodiments of FIGS. 3A and 3B, the instrument 16 includes a guiding slot 41 extending between a suitably chosen portion of the elongate body 38 and a distal edge 43 thereof. The guiding slot 41 is configured to receive an element of the spinal stabilization system such as the connecting element 18 (FIG. 1) and guide it toward the top portion 24 of the vertebral anchor 14, such that it can be secured against surfaces of the top portion 24. Moreover, the guiding slot 41 may facilitate bending of the elongate body 38 such that a natural compressive force can be applied against engaging surfaces of the top portion 24, which enhances axial engagement of the instrument 16 with the vertebral anchor 14.

With reference to FIG. 3B and unlike the exemplary instrument of FIG. 3A, the protrusions 60 of FIG. 3B extend outward of or beyond a perimeter 38a of the elongate body 38. Additionally, a tubular member 39 can be placed over the elongate body 38 to restrict radially outward movement or splaying of the distal end 42 of the instrument 16. In this regard, accordingly, the tubular member 6o may permit a relatively high force to be applied to against the vertebral anchor 14 with a minimal or negligible likelihood of splaying of the distal end 42 of the instrument 16. The instrument of FIG. 3B also includes a guiding slot 40 that includes a tapered region 41a that may improve the installation of the connecting element 18 to the vertebral anchor 14.

While the exemplary instrument 16 is depicted including a generally uniaxial elongate body 38 that does not extend beyond the footprint of the vertebral anchor 14, it is contemplated that it may alternatively have other shapes and footprints. Accordingly, an instrument may include an elongate body having one or more curved segments or an elongate body having more than one uniaxial segments. These variations may be suitably chosen, for example, to facilitate actuation of the instrument to rotate the vertebral anchor 14.

Figure 4:
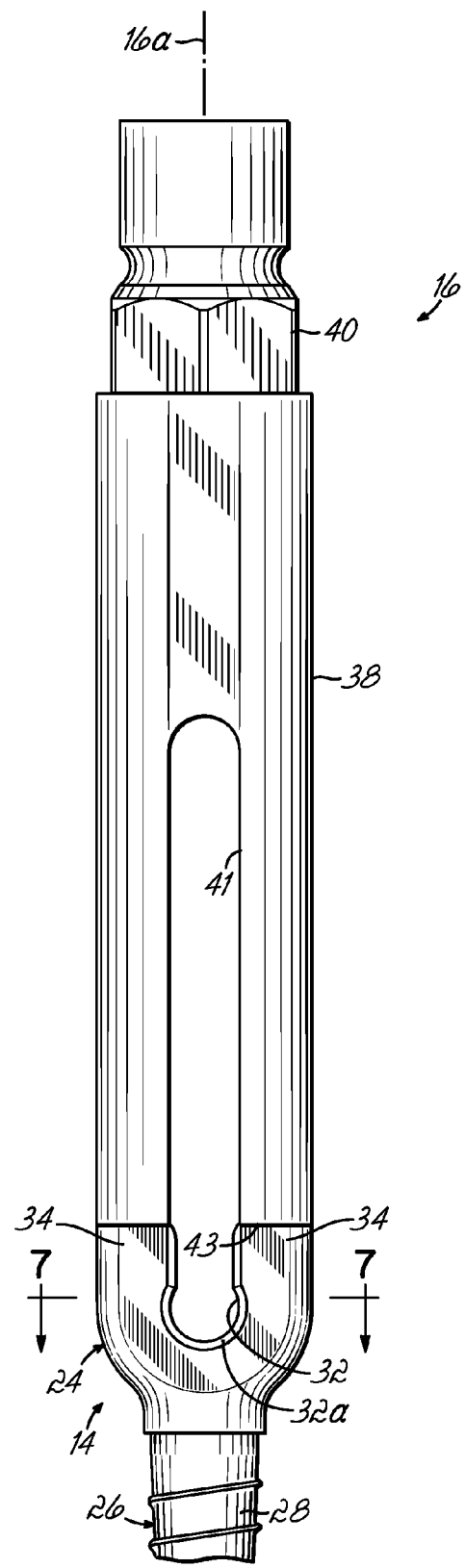
FIG. 4 is a partial elevational view of the vertebral anchor and instrument respectively of FIGS. 2-3A, in a coupled state.

With reference to FIGS. 1-7, and as mentioned above, the installation system 10 in one embodiment includes an interface between the vertebral anchor 14 and the instrument 16 to facilitate suitable engagement there between. When in an engaged state, the vertebral anchor 14 and instrument 16 are generally as depicted in FIG. 4. To this end, the interface is defined by cooperating features of the top portion 24 of the vertebral anchor 14 and distal end 42 of the instrument 16. Accordingly, and with particular reference to the embodiment of FIGS. 5 and 7, the vertebral anchor 14 includes, at its top portion 24 a pair of first engaging elements in the form of female elements or slots 44 on each side of the longitudinal axis 30 (FIG. 2) of the top portion 24. More specifically for this embodiment, each of the slots 44 is trapezoidal and extends along a longitudinal axis 44a thereof (generally perpendicular to the plane of FIG. 5) and defines the shape of each of the walls 34 of the top portion 24. Each of the female slots 44 includes an interior wall 46 and inwardly diverging lateral walls 48 jointly defining the shape of the exemplary first engaging element of the embodiment of FIGS. 1-7.

In one aspect of the shown exemplary embodiment, each of the female slots 44 extends from a perimeter 50 of the top portion 24 and toward the longitudinal axis 30. As used herein, the term perimeter is intended to include, in addition to the physically ascertainable outer surfaces defining the shape of the top portion 24, a pair of projected surfaces 50a, illustrated in phantom (FIG. 5), and defined by corresponding projections of the outer surfaces 50b of the walls 34. The perimeter 50, accordingly, extends around the axis 30 of the top portion 24. While the exemplary embodiment of FIGS. 1-7 depicts a pair of first engaging elements radially equidistant from the axis 30, it is contemplated that the first engaging elements may alternatively not be equidistant from the axis 30. Similarly, it is contemplated that a specific embodiment of a vertebral anchor (not shown) may alternatively include first engaging elements in a number less than or in excess of two.

With reference to FIGS. 3-7 and as described above, the interface between the vertebral anchor 14 and the instrument 16 includes a feature on the distal end 42 of the instrument 16 that cooperates with the top portion 24 of the vertebral anchor 14 to provide engagement therewith. To this end, a pair of second engaging elements in the form of male elements or protrusions 60 integrally extend from the distal edge 43 of the distal end 42. More specifically, the protrusions 60 in one embodiment protrude in a direction generally parallel to a longitudinal axis 16a (FIGS. 3A and 3B) of the instrument 16 and are positioned to be in registration with the trapezoidal female slots 44 of the vertebral anchor 14.

In the exemplary shown embodiment, the protrusions 60 are generally trapezoidal in shape (FIG. 6) such that a tight engagement is provided with the female slots 44. Tight engagement of the female slots 44 with the protrusions 60, as depicted in FIG. 4, facilitates substantial restriction of the top portion 24 of the vertebral anchor 14 and the instrument 16 from rotational movement, relative to one another, about axis 30 of the top portion 24. In one aspect of this embodiment, the amount of rotational restriction of the top portion 24 relative to the instrument 16 may be controlled by a suitably chosen clearance between the lateral walls 48 of each of the female slots 44 and correspondingly confronting surfaces of the protrusions 60. This clearance may, for example be in the range of about 0.0019 mm to about 0.0486 mm. Accordingly, this rotational restriction limits the application of unnecessary torque and resulting shear stress on the elongate body 38 as the instrument 16 is actuated i.e., rotated.

In one aspect of the shown exemplary embodiment, each of the protrusions 60 includes a tapered end 66 to facilitate insertion of the protrusion 60 into the female slot 44. Persons of ordinary skill in the art will readily appreciate that the instrument 16 may include a number of protrusions 60 that is less than or in excess of two. Similarly, the number of protrusions 60 may alternatively be in a number that is different from the number of female slots 44 of the vertebral anchor 14.

Figure 7:
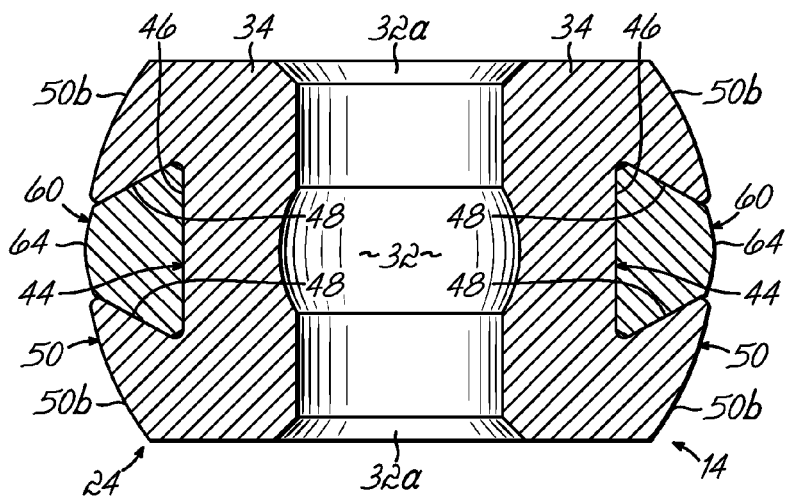
FIG. 7 is a cross-sectional view taken along line 7-7 of FIG. 4.

With particular reference to FIGS. 4 and 7, engagement of the instrument 16 with the vertebral anchor 14 is such that each of the female slots 44 slidably receives a corresponding protrusion 60 with a motion generally parallel to the axes 16a and 30, respectively of the instrument 16 and top portion 24. In one aspect of this motion, it may be such that each of the protrusions 60 remains substantially within the perimeter 50 of the top portion 24. More particularly, this motion may be such that the outer surface 64 of each protrusion 60 coincides with a corresponding projected surface 50a or inboard therefrom (i.e. closer to the axis 30). The motion may further be such that a majority of the cross-sectional area (FIG. 6) of the protrusion 60 falls within the perimeter 50. In some embodiments, the protrusion 60 entirely falls within the perimeter 50 allowing for the perimeter of the instrument 16 to match the perimeter 50 of the vertebral anchor 14.

In the engaged state of FIGS. 4 and 7, accordingly, each of the protrusions 60 extends substantially within the perimeter 50 of the top portion 24 i.e., a majority of the cross-sectional area of the protrusion 60 falls within the perimeter 50. In one aspect of this exemplary engaged state, the distal edge 43 of the instrument 16 provides alone, or in combination with the tapered ends 66 of the protrusions 60, an axial stopping point in the engagement of the instrument 16 with the vertebral anchor 14.

In another aspect of this exemplary engaged state, the likelihood of rotational disengagement between the instrument 16 and vertebral anchor 14 is minimal or negligible. Moreover, by providing for a tight fit between the protrusions 60 and female slots 44, the transfer of torque to the vertebral anchor 14 is facilitated. More particularly, torque applied at the gripping portion 40 of the instrument 16 is effectively transferred to the vertebral anchor 14, which allows the instrument to have a relative long elongate body 38.

While the exemplary instrument 16 of FIGS. 3A, 3B and 6-7 is depicted including two protrusions 60 that are equidistant from the axis 16a of the instrument 16, persons of ordinary skill in the art will readily appreciate that the protrusions 60 may alternatively be of any number and not be equidistant from the axis 16a.

While FIGS. 2-7 depict an exemplary embodiment as described above, it is contemplated that deviations from such embodiment can be reasonably made, alone or in combination. For example, and without limitation, the interface between the instrument 16 and vertebral anchor 14 may be such that the first engaging elements of the vertebral anchor 14 are in the form of male elements or protrusions as generally described above and the second engaging elements are in the form of female slots. Similarly, an interface may be such that any two of the first or second engaging elements described above may differ from one another. Accordingly, for example, and without limitation, a vertebral anchor may include a pair of first engaging elements of which one is trapezoidal in shape and the other is rectangular. In another specific embodiment, moreover, one or more of the first engaging elements (e.g., the trapezoidal female slots) may alternatively be completely enclosed within a perimeter of a top portion of the vertebral anchor, and therefore not define any portions of such perimeter. In other embodiments, the protrusions and female slots may be of a different shape such as round or square.

Figure 8:
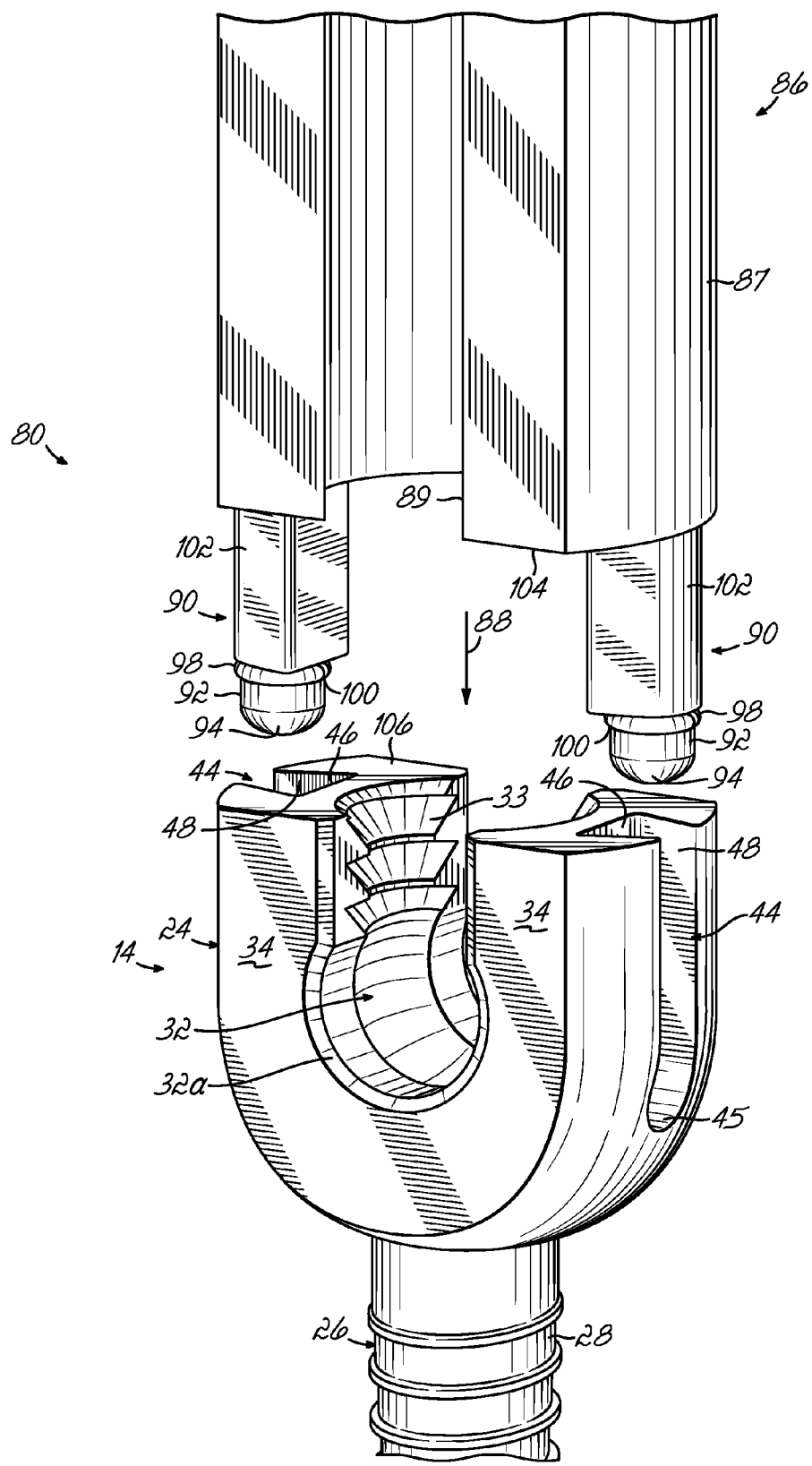
FIG. 8 is a partial perspective view of another embodiment of a vertebral anchor and corresponding instrument prior to coupling.
Figure 9:
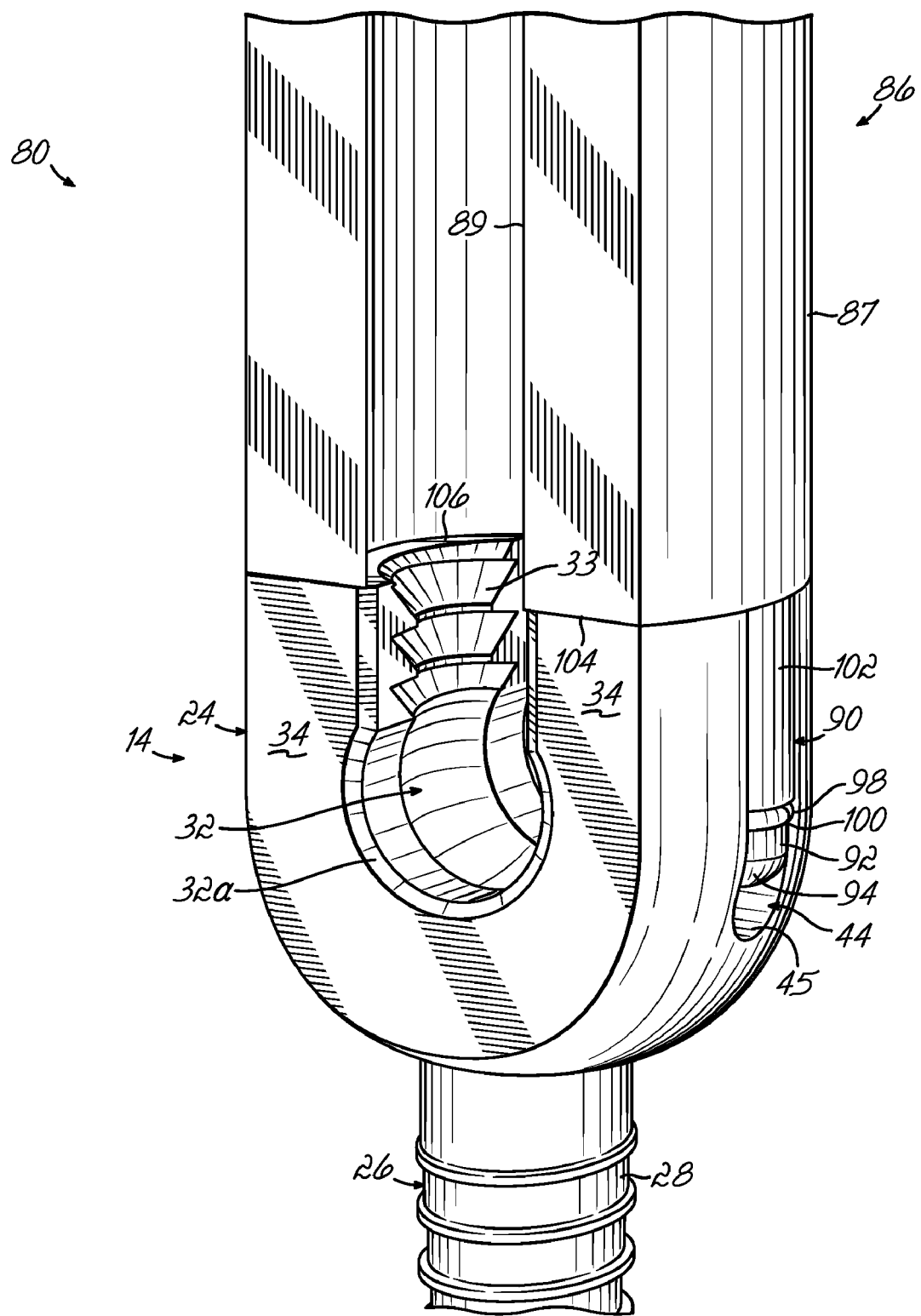
FIG. 9 is a partial perspective view of the vertebral anchor and instrument of FIG. 8 in a coupled state.

With reference to FIGS. 8-9, in which like numerals refer to like features of FIGS. 2-7, another embodiment of an installation system 80 for implantation of a spinal stabilization system is shown. The installation system 80 is similar in most respects to the embodiment of FIGS. 2-7, the description of which may be referred to for an understanding of the embodiment of FIGS. 8-9 as well. The installation system 80 includes a vertebral anchor 14 in the form of a pedicle screw having a shank 26 and a top portion 24 that is engaged by an instrument 86 similar in most respects to the instrument 16 of FIGS. 3-4 and 6-7. Accordingly, the instrument 86 includes an elongate body 87 and a guiding slot 89. The vertebral anchor 14 includes a pair of first engaging elements in the form of female slots 44 that defines an interface with the instrument 86. In one aspect of this embodiment, engagement motion is similar also to that described above for the embodiments of FIGS. 2-7 and follows the general direction of arrow 88.

The instrument 86 includes a pair of second engaging elements in the form of male elements or protrusions 90 disposed to be in registration with and closely matching the cross-sectional shape of the female slots 44. Each of the protrusions 90 includes, at a distal end thereof, fingers 92 having a tapered end 94 to facilitate insertion into the female slot 44. Each of the exemplary fingers 92 is depicted having a generally cylindrical shape i.e., having a circular cross-sectional shape, although other shapes are contemplated as well. For example, and without limitation, the fingers 92 may alternatively have a square, rectangular or polygonal cross-sectional shape. Likewise, the tapered end 94 is depicted having a convex shape, although other shapes including or not including arcuate segments are contemplated as well.

With continued reference to FIGS. 8-9, and in one aspect of the shown embodiment, each finger 92 includes a outwardly extending member in the form of a ring member 98 disposed about a reference axis (not shown) of the finger 92 and positioned proximate a base portion 100 of the finger 92. The ring member 98 may be coupled to or, alternatively, integral with other portions of the finger 92 or main body 102 of the protrusion 90. In another aspect of this embodiment, the ring member 98 may include a resilient structure such that it takes the form of an outwardly biasing member. Moreover, the ring member 98 may be shaped to protrude radially beyond the plane defined by the outer surfaces of the main body 102.

In operation, and during engagement of the instrument 86 with vertebral anchor 14 as indicated by the arrow 88 (FIG. 8), the ring member 98 may provide additional guidance into the female slot 44. More particularly, the exemplary ring member 98, by protruding beyond the plane defined by the outer surfaces of the main body 102, creates a tight fit between a protrusion 90 and a corresponding female slot 44, thereby guiding the protrusion 90 into the female slot 44 along a relatively narrow path.

The shape, relative dimensions and material defining the ring members 98 may be such that a relatively large level of frictional engagement is created between the protrusions 90 and female slots 44. Accordingly, the ring member 98 may facilitate axial retention of the protrusion 90 of which it is part within the corresponding female slot 44. This retention is in addition to the rotational restriction described above for the embodiment of FIGS. 2-7 and which is applicable to the installation system 80 of FIGS. 8-9 as well.

With particular reference to FIG. 9, the installation system 80 is shown in an engaged state. In this exemplary state, a distal surface 104 of the instrument 86 provides an axial stopping point of the instrument 86 relative to the vertebral anchor 14, when in contact with an upper surface 106 thereof Moreover, the tapered ends 94 are shown not being in contact with a base surface 45 of the female slots 44. Persons of ordinary skill in the art will readily appreciate that, alternatively, the tapered ends 94 may alone, or in combination with the distal surface 104, provide an axial stopping point of the instrument 86 relative to the vertebral anchor 14.

Variations of the exemplary embodiment of FIGS. 8-9 are contemplated. These variations may include, without limitation, any of the exemplary variations, alone or in combination, made in regard to any of the above embodiments or features thereof.

Figure 10:
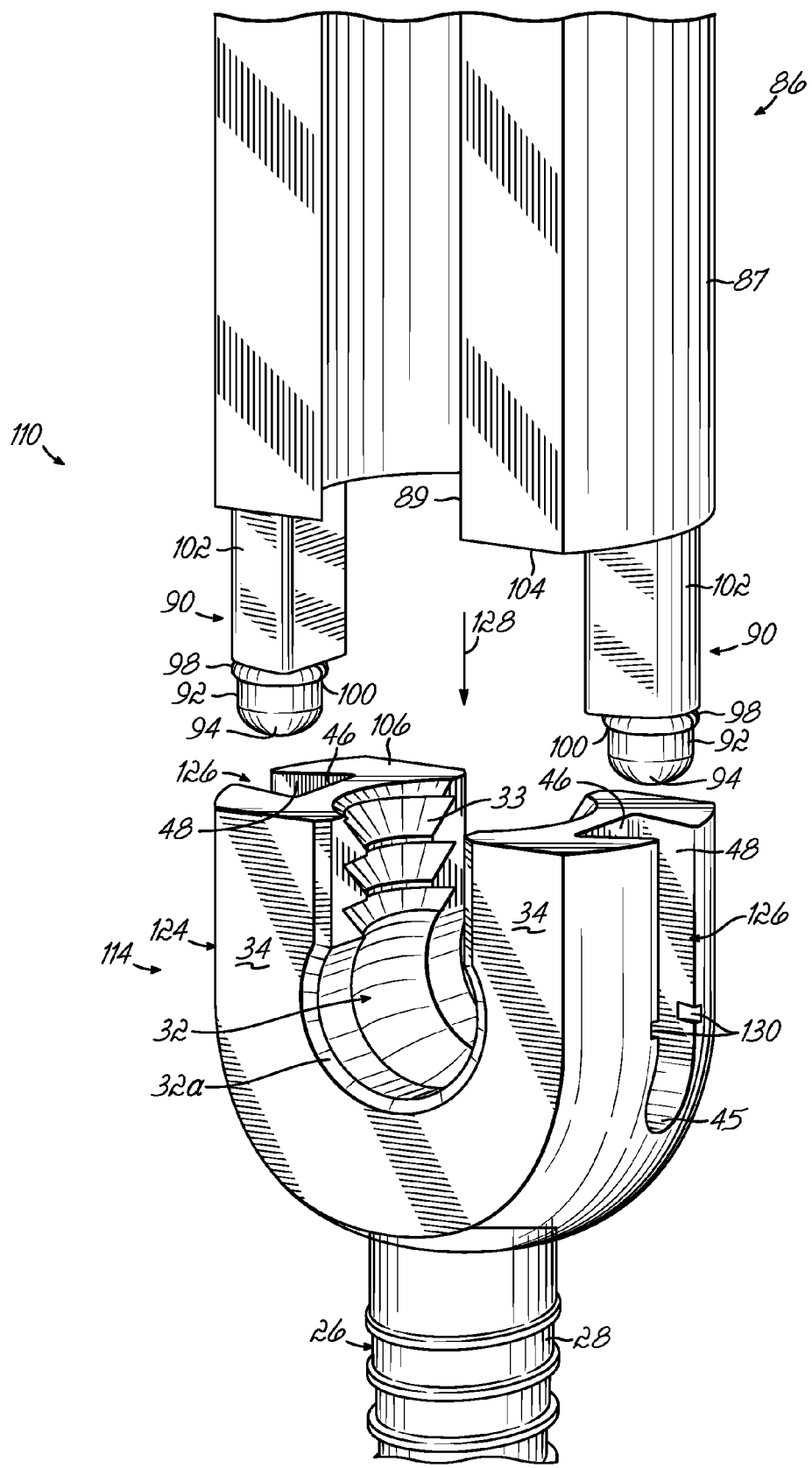
FIG. 10 is a partial perspective view of yet another embodiment of a vertebral anchor and corresponding instrument prior to coupling.
Figure 11:
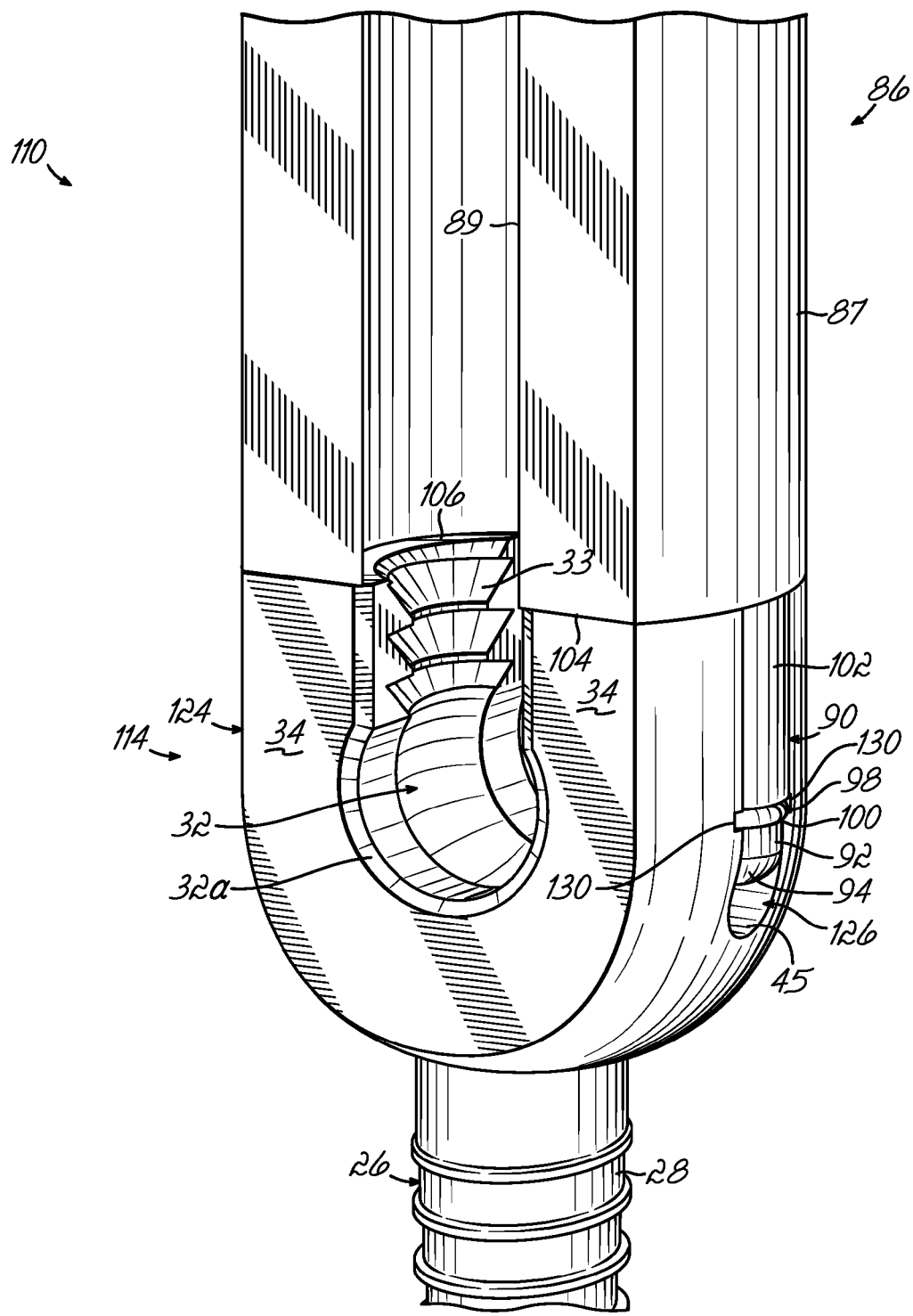
FIG. 11 is a partial perspective view of the vertebral anchor and instrument of FIG. 10 in a coupled state.

With reference to FIGS. 10-11, in which like reference numerals refer to like features of FIGS. 2-9, an alternative embodiment of an installation system 110 for implantation of a spinal stabilization system is shown. The installation system 110 is similar in most respects to the embodiment of FIGS. 8-9, the description of which may be referred to for an understanding of the embodiment of FIGS. 10-11 as well. The installation system 110 includes a vertebral anchor 114 in the form of a pedicle screw having a shank 26 and a top portion 124 that is engaged by an instrument 86 similar in most respects to the instrument 86 of FIGS. 8-9. Accordingly, the instrument 86 includes an elongate body 87 and a guiding slot 89. The vertebral anchor 114 includes a pair of first engaging elements in the form of female slots 126 that define an interface with the instrument 86. In one aspect of this embodiment, engagement motion is similar also to that described above for the embodiments of FIGS. 8-9 and follows the general direction of arrow 128.

The female slots 126 of the top portion 124 are similar in most respect to the female slots 44 of FIGS. 8-9 but include one or more recesses 130 configured to receive the ring member 98 therein. More particularly, each recess 130 is configured alone, or in combination with other recesses 130, to receive all or at least a portion of the ring member 98.

With particular reference to FIG. 11, in which the installation system 110 is shown in an engaged state, the ring member 98 is depicted occupying the volume defined by each of the recesses 130, thereby establishing an axial position of the instrument 86 relative to the vertebral anchor 114 (i.e., an axial position of the protrusions 90 relative to the female slots 126). Moreover, engagement of the ring member 98 within the recesses 130 facilitates axial retention of the protrusions 90 within the female slots 126. Accordingly, engagement of the ring member 98 within the recesses 130 enhances axial stability of the instrument 86 relative to the vertebral anchor 114.

In one aspect of this embodiment, and as described above with reference to the embodiment of FIGS. 8-9, the ring member 98 may include a resilient structure such that the ring member 98 takes the form of an outwardly biasing member. This resiliency may further be such that the ring member 98 is pushed inwardly (i.e., toward the reference axis of the finger 92) as the protrusion 90 and, more specifically, the finger 92 travels along surfaces defining the female slot 126. Moreover, this resiliency may be such that the ring member expands outwardly when exposed to the recesses 130.

With continued reference to FIGS. 10-11, while the shown embodiment depicts a female slot 126 including at least two recesses 130, it is contemplated that a first engaging element in the form of a female slot or any other suitable form may include recesses in any number. For example, and without limitation, a first engaging element may include only one recess that extends along a relatively large portion of the surfaces defining the female slot 126. Other variations may include, without limitation, any of the exemplary variations, alone or in combination, made in regard to any of the above embodiments or features thereof.

Figure 12:
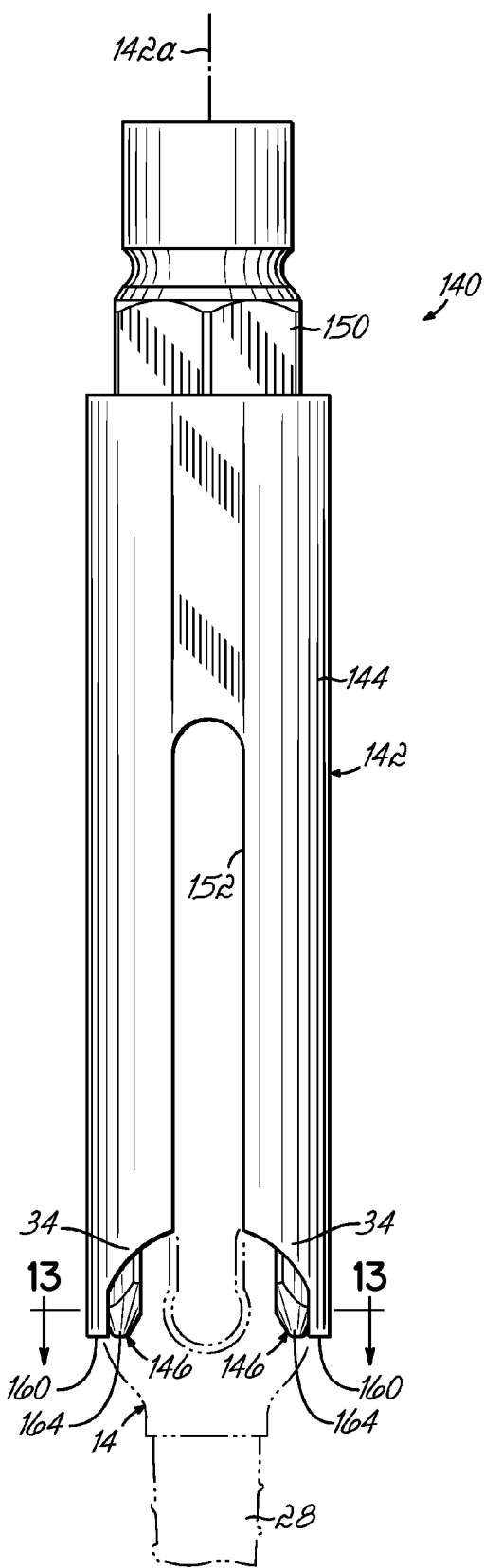
FIG. 12 is an elevational view of another embodiment of an instrument of a spinal fixation installation system.
Figure 13:
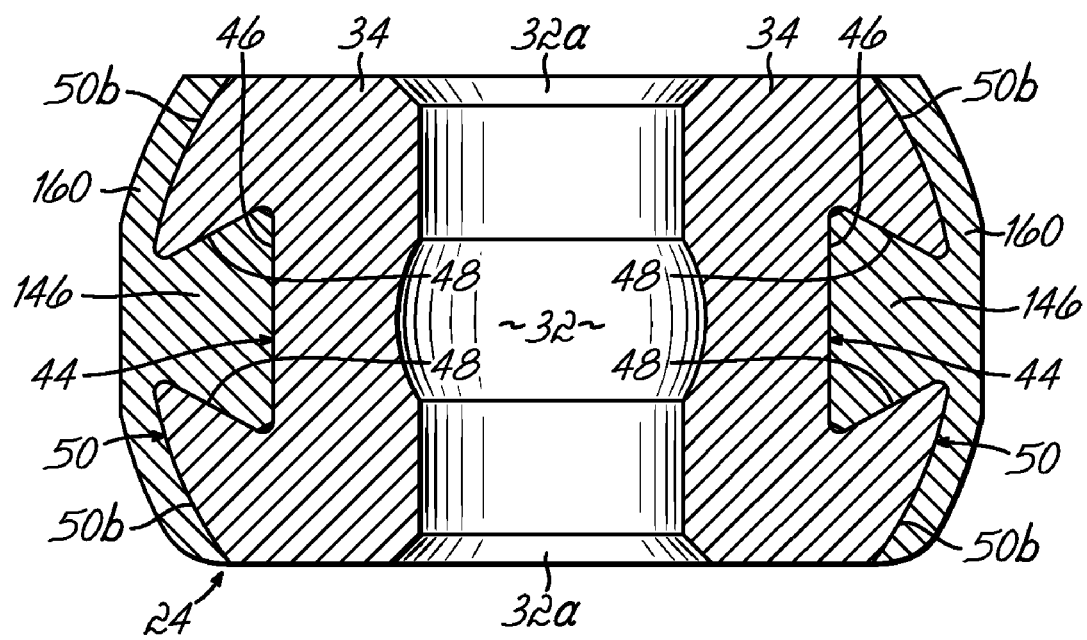
FIG. 13 is a cross-sectional view taken along line 13-13 of FIG. 12.

With reference to FIGS. 12-13, in which like reference numerals refer to like features of the embodiment of FIGS. 2-7, another embodiment of an installation system 140 is similar in most respects to the installation system 10 of FIGS. 2-7, the description of which may be referred for an understanding of the installation system 140 as well.

The installation system 140 includes a vertebral anchor 14 shown in phantom (FIG. 12) and which has a top portion 24 that includes a pair of first engaging elements in the form of female slots 44. An instrument 142 having an elongate body 144 and a pair of second engaging elements in the form of male elements or protrusions 146 permit engagement of the vertebral anchor 14 such that it may be actuated into engagement with a vertebra (FIG. 1). The instrument 142 further includes an actuator in the form of a gripping portion 150, a guiding slot 152, both of which are respectively similar in most respects to the gripping portion 40 and guiding slot 152 of FIG. 3, the description of which may be referred to for an understanding of these features as well.

In the exemplary embodiment of FIGS. 12-13, the protrusions 146, which are similar in most respects to the protrusions 90 of FIGS. 3A and 3B, are surrounded by a pair of projections or shields 160. The shields 160 are disposed radially outward from or beyond (i.e., relative to an axis 142*a* of the instrument 142) the protrusions 146. More particularly, and with particular reference to FIG. 13, the protrusions 146 and shield 160 may form a continuous body at a point away from the distal surfaces 164 of the protrusions 146. In this regard, accordingly, each of the protrusions 146 and corresponding shield 16o become separate components at least at a point proximate the distal surfaces 164. In one aspect of this embodiment, and still referring to the view of FIG. 13, a protrusion 146 and corresponding shield 160 may be integrally formed or alternative coupled to one another. FIG. 13 depicts an integral protrusion 146 and shield 16o construction. Alternatively, the instrument 142 can be movable along the axis 142a of the instrument 142 and, thus, not of an integral construction.

With reference to FIGS. 12-13, the shields 160 are disposed outside of the perimeter 50 of the top portion 24 of the vertebral anchor. Operationally, the shields 16o restrict radially outward movement or splaying of the protrusions 146. In this regard, accordingly, the shields 16o may permit a relatively high force to be applied to against the vertebral anchor 14 with a minimal or negligible likelihood of splaying of the protrusions 146.

Variations of the exemplary embodiment of FIGS. 12-13 are contemplated. These variations may include, without limitation, any of the exemplary variations, alone or in combination, made in regard to any of the above embodiments or features thereof.

Figure 14:
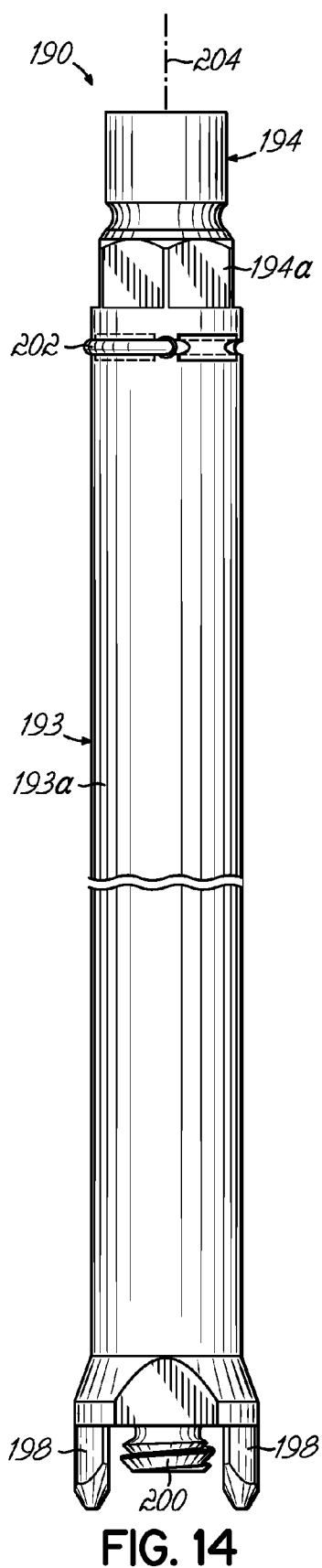
FIG. 14 is a partial elevational view of another embodiment of an instrument of a spinal fixation installation system.
Figure 15:
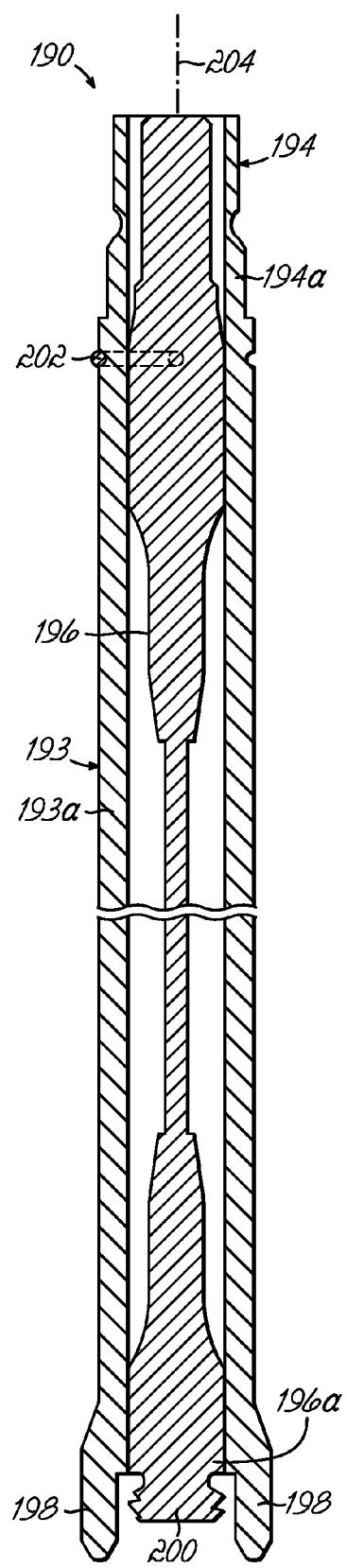
FIG. 15 is a cross-sectional view of the instrument of FIG. 14.

With reference to FIGS. 14-17, different exemplary embodiments of instruments of installation systems in accordance with the above embodiments are depicted. With reference to FIGS. 14-15, an embodiment of an instrument 190 includes an actuator 194 that includes a polygonal gripping portion 194a, as well as a guide wire 196. The guide wire may also include a hole or cannulation through its center to accommodate a K-wire that may be used in a minimally invasive procedure. The instrument 190 further includes a pair of protrusions 198 similar in most respects to the protrusions 178 of the exemplary instruments 16 of FIGS. 3A and 3B and which are suitably designed to engage corresponding portions of a vertebral anchor. In one aspect of this embodiment, and unlike the embodiments depicted in FIGS. 2-13, the instrument 190 includes a substantially continuous tubular structure or cannula 193 defined by walls 193a of the instrument 190.

The exemplary instrument 190 includes, as mentioned above, a guide wire 196 (e.g., a flexible guide wire), which is disposed within the cannula 193. Moreover, a securing member 200 in the form of a set screw is coupled to a distal end 196a of the guide wire 196. Operationally, the protrusions 198 engage and rotate a vertebral anchor in ways as described with regard to the embodiments of FIGS. 2-13. For example, the actuator 194 may be rotated by gripping the gripping portion 194a thereof with a suitable tool such as a wrench, which in turn causes rotation of the vertebral anchor, which thereby engages a vertebra.

In one aspect of the embodiment of FIGS. 14-15, the guide wire 196 is held in a fixed rotational position relative to the cannula 193. More specifically, a retaining structure 202 in the form of a retaining spring or clip is coupled to the guide wire 196 and the cannula 193, thereby restricting rotation of the guide wire 196 relative to the cannula 193. Accordingly, actuation (e.g., rotation) of the instrument 190, for example by gripping and rotating the gripping portion 194a, similarly causes rotation of the guide wire 196.

With continued reference to the embodiment of FIGS. 14-15, a subsequent step in the installation of a spinal stabilization system may involve decoupling of the retaining clip 202 from the cannula 193 and guide wire 196, such that the guide wire 196 may be rotated independently from the cannula 193. More particularly, the rotational position (i.e., about a longitudinal axis 204 of the cannula 193) of the cannula 193 may be held constant by engagement with the implanted anchor (not shown) and the guide wire 196 rotated to cause rotation of the securing member 200 coupled to the distal end 196a of the guide wire 196. Rotation of the securing member 200, in turn, engages a corresponding surface of the vertebral anchor, such as, for example a threaded region similar to the threaded region 33 of the embodiment of FIGS. 5 and 7. Engagement of a threaded region as described above secures the securing member 200 against the vertebral anchor and may further secure a spinal fixation connecting element 78 against the vertebral anchor.

The securing member 200 may subsequently be decoupled from the guide wire 196 and the guide wire 196 removed from within the cannula 193 or, alternatively, the guide wire 196 and the other portions of the instrument 190 may be jointly removed from the surgical site i.e., away from the vertebral anchor. In one aspect of the exemplary embodiment of FIGS. 14-15, coupling of the securing member 200 to the guide wire 196 may take the form of a releasable coupling known to those of ordinary skill in the art. For example, and without limitation, this coupling may include engaging cooperating surfaces of the distal end 196a and securing member 200 and/or include a frangible connection.

In other embodiments, the guide wire 196 can be eliminated from the instrument 190 allowing for access to the vertebral anchor 14 through the cannula 193. In this embodiment, a securing element such as a set screw (not shown) may be passed through the cannula 193 to the vertebral anchor 14 for securing a connecting element 18. For example, the set screw may be engaged by the hex end of a driver and then passed into the cannula 193 with the handle of the driver extending outside of and beyond the gripping portion 194 of the instrument 190.

Figure 16:
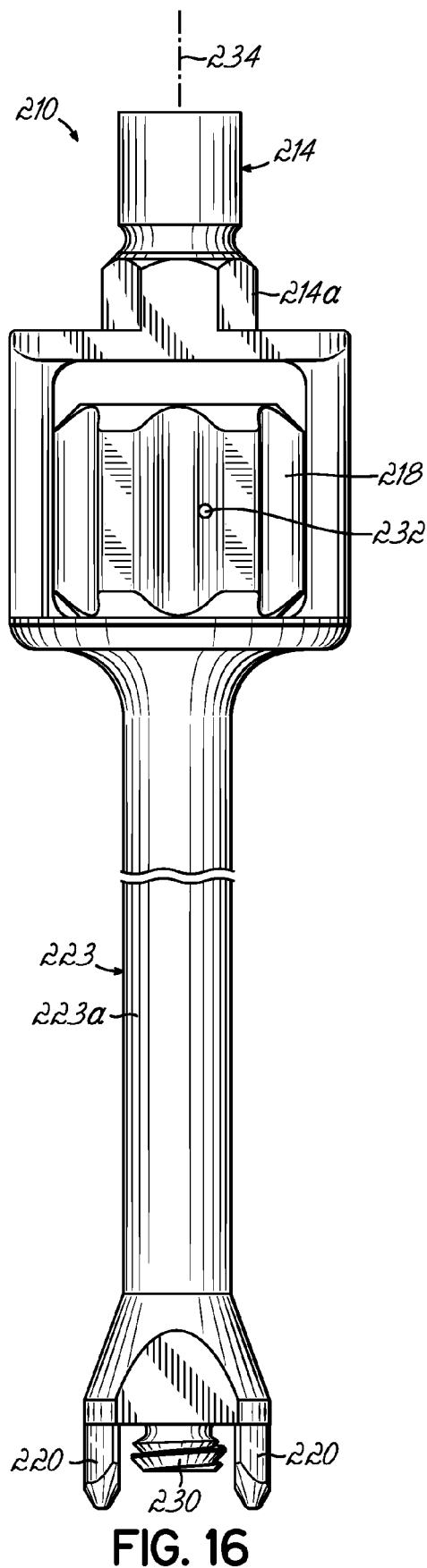
FIG. 16 is a partial elevational view of another embodiment of an instrument of a spinal fixation installation system.
Figure 17:
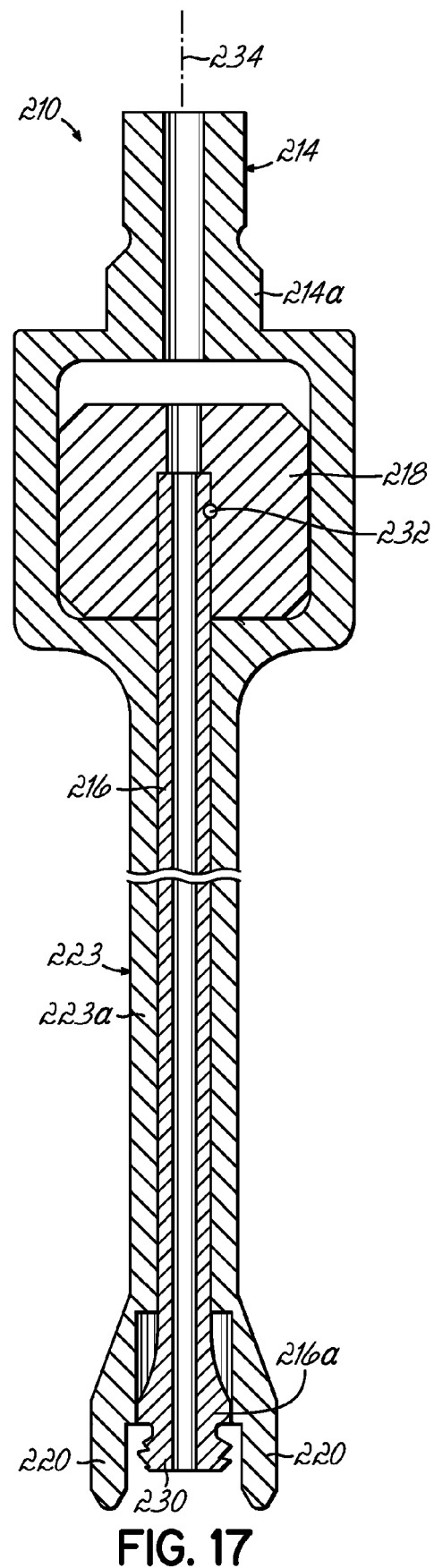
FIG. 17 is a cross-sectional view of the instrument of FIG. 16.

With reference to FIGS. 16-17, an alternative embodiment of an instrument 210 includes a cannula actuator 214 that includes a polygonal gripping portion 214a, as well as a guide wire 216 and corresponding guide wire actuator 218. The guide wire may also include a hole or cannulation through its center to accommodate a K-wire that may be used in a minimally invasive procedure. The instrument 210 further includes a pair of protrusions 220 similar in most respects to the protrusions 178 of the exemplary instruments 16 of FIGS. 3A and 3B and which are suitably designed to engage corresponding portions of a vertebral anchor (not shown). In one aspect of this embodiment, and similar to the instrument 190 depicted in FIGS. 14-15, the exemplary instrument 210 includes a substantially continuous tubular structure or cannula 223 defined by walls 223a of the instrument 210.

The exemplary instrument 210 includes, as mentioned above, a guide wire 216 (e.g., a flexible guide wire), which is disposed within the cannula 223. Moreover, a securing member 230 in the form of a set screw is coupled to a distal end 216a of the guide wire 216. Operationally, the protrusions 220 engage and rotate a vertebral anchor in ways as described with regard to any of the above embodiments (FIGS. 2-15). For example, the cannula actuator 214 may be rotated by gripping the gripping portion 214a thereof with a suitable tool such as a wrench, which in turn causes rotation of the vertebral anchor, which thereby engages a vertebra.

In one aspect of the embodiment of FIGS. 16-17, the guide wire 216 is held in a fixed rotational position relative to the cannula 223. More specifically, a retaining structure 232 in the form of a retaining pin extends through and couples the guide wire 216 and the cannula 223, thereby restricting rotation of the guide wire 216 relative to the cannula 223. Accordingly, actuation (e.g., rotation) of the instrument 210, for example by gripping and rotating the gripping portion 214a, similarly causes rotation of the guide wire 216.

With continued reference to the exemplary embodiment of FIGS. 16-17, a subsequent step in the installation of a spinal stabilization system may involve decoupling of the retaining structure 232 from the cannula 223 and guide wire 216, such that the guide wire 216 may be rotated independently from the cannula 223. More particularly, the rotational position (i.e., about a longitudinal axis 234 of the cannula 223) of the cannula 223 may be held constant by engagement with the implanted vertebral anchor (not shown) and the guide wire 216 rotated to cause rotation of the securing member 230 coupled to the distal end 216a of the guide wire 216. Rotation of the guide wire 216 may be effected by suitably rotating the guide wire actuator 218. Rotation of the securing member 230, in turn, engages a corresponding surface of the vertebral anchor, such as, for example a threaded region similar to the threaded region 33 of the embodiment of FIGS. 5 and 7. Engagement of a threaded region as described above secures the securing member 230 against the vertebral anchor and may further secure a spinal fixation connecting element 18 against the vertebral anchor.

The securing member 230 may subsequently be decoupled from the guide wire 216 and the guide wire 216 removed from within the cannula 223 or, alternatively, the guide wire 216 and the other portions of the instrument 210 may be jointly removed from the surgical site i.e., away from the vertebral anchor. In one aspect of the exemplary embodiment of FIGS. 16-17, coupling of the securing member 230 to the guide wire 216 may take the form of a releasable coupling known to those of ordinary skill in the art. For example, and without limitation, this coupling may include engaging cooperating surfaces of the distal end 216a and securing member 230 and/or include a frangible connection.

Figure 18:
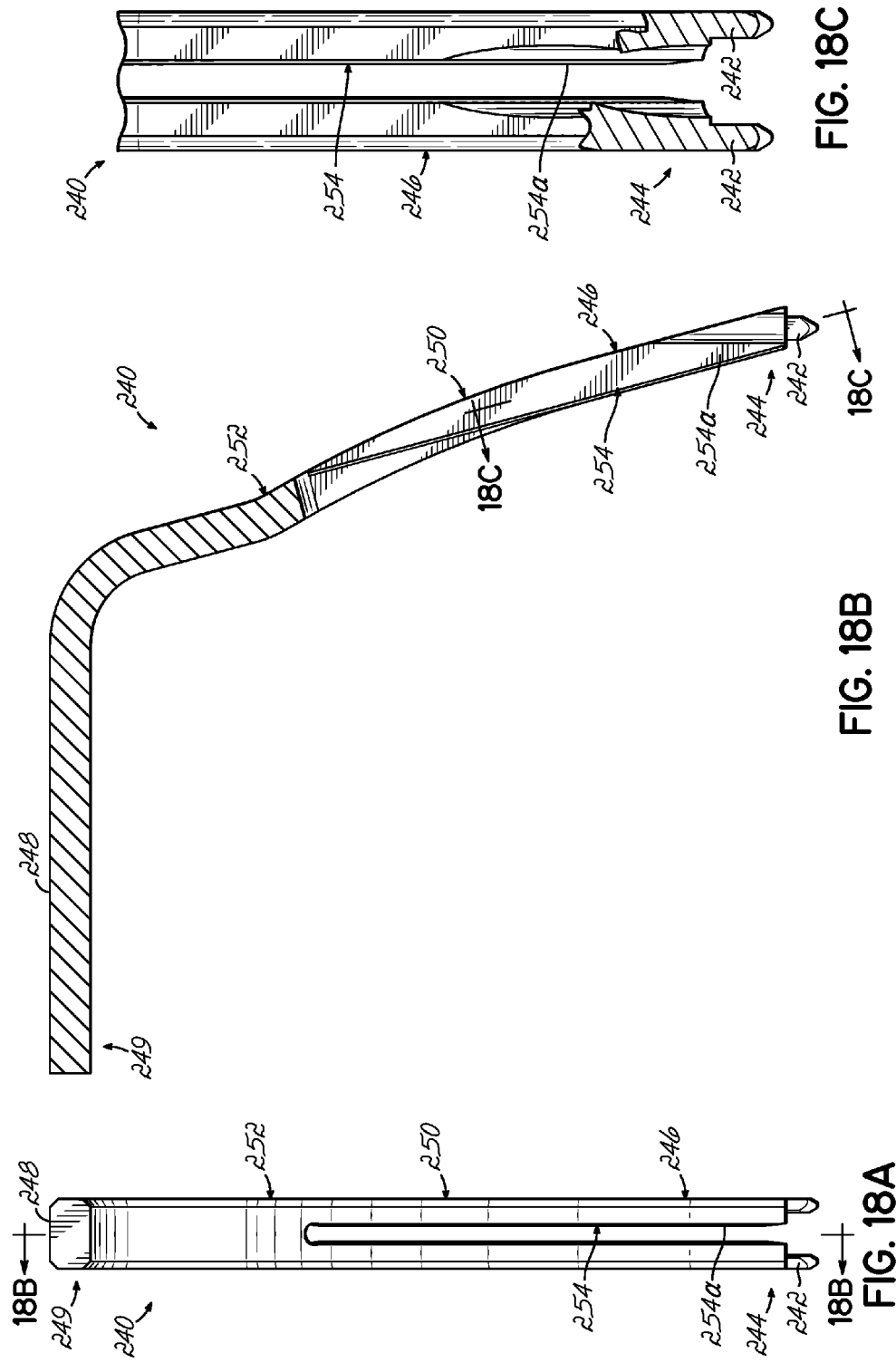
FIG. 18A is an elevational view of another embodiment of an instrument of a spinal fixation installation system.
FIG. 18B is a cross-sectional view taken along line 18B-18B of FIG. 18A.
FIG. 18C is a partial cross-sectional view taken along line 18C-18C of FIG. 18B.

Referring now to FIGS. 18A-21, use of instruments 240 to install components of the spinal stabilization system 12 to the vertebrae 17 of a spine will now be described. With reference to FIGS. 18A-C, the exemplary instrument 240 includes protrusions 242 at a distal end 244, which are similar in most respects to the protrusions 90 of FIGS. 3A and 3B. The instrument 240 also includes a substantially straight portion 246 at the distal end 244 and a substantially straight handle portion 248 at a proximal end 249 of the instrument 240. Between the proximal end 249 and the distal end 244, the instrument 240 includes a first curved portion 250 and second curved portion 252 shaped to facilitate the installation of a flexible element 19 between the vertebral anchors 14. The instrument of FIGS. 18A-C also includes a guiding slot 254 that includes a tapered region 254a that may improve the installation of a connecting element 18 between vertebral anchors 14. The instrument 240 can be formed of a rigid material such as metal or can be constructed in whole or part with one or more flexible materials.

Figure 19:
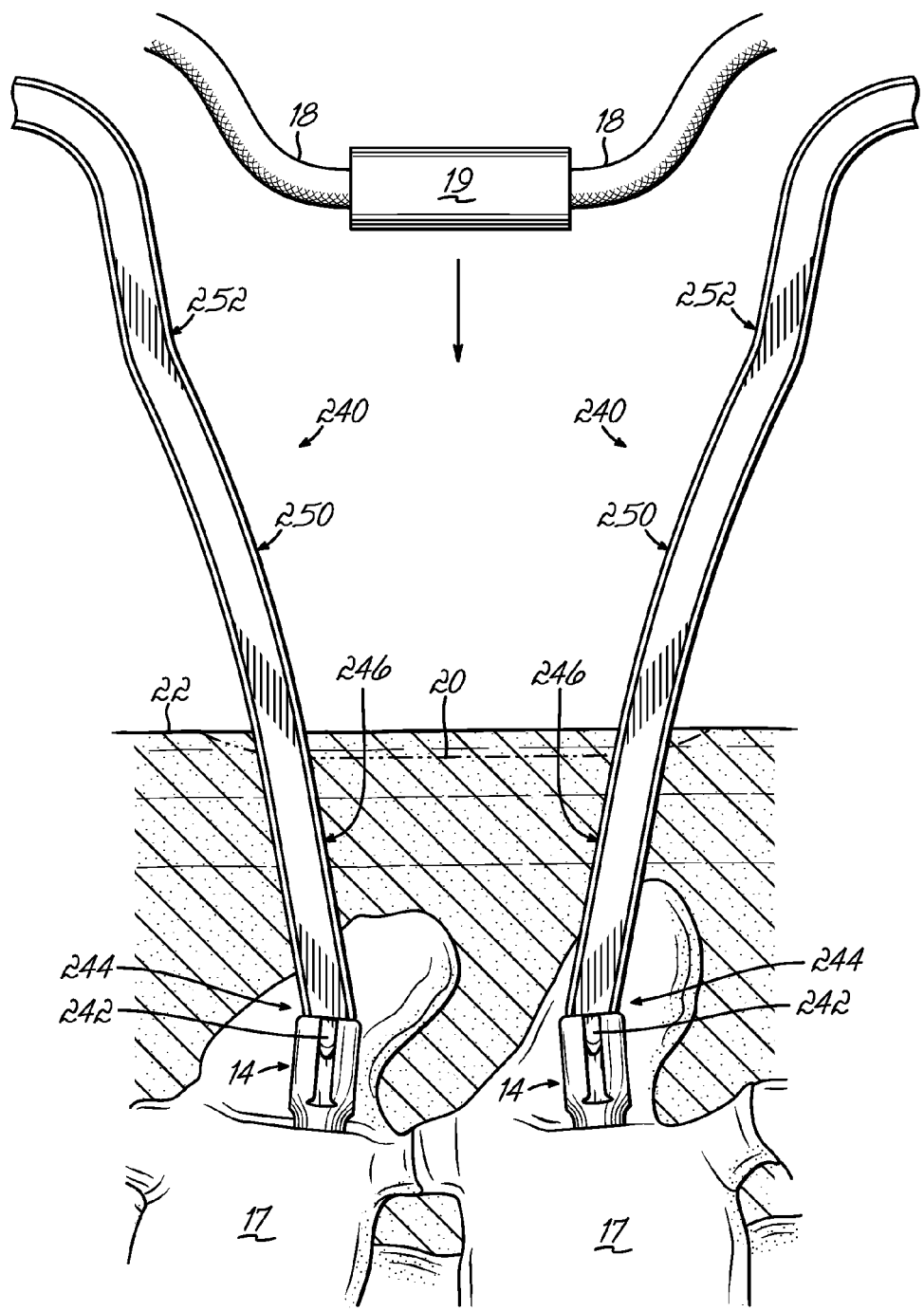
FIG. 19 is a perspective view of instruments of FIGS. 18A-C being used to engage anchors installed into a region of a spine and a flexible member and a connecting element positioned above the instruments.

With reference to FIG. 19, the connecting element 18 and flexible member 19 are coupled together and positioned above the instruments 240 and then moved down in a direction toward the spine. The instruments 240 can be coupled together in an open procedure to provide a guide for the insertion of a connecting element 18 and a flexible member 19 like instruments 16 are coupled to the vertebral anchors 14 in FIG. 1. In other embodiments, the instruments 240 can be positioned so the substantially straight portion 246 at the distal end 244 of each of the instruments are parallel. This configuration may be used in more minimally invasive procedures that use retractor or portal systems. In another embodiment, the instrument 240 can be configured without curved portions 250, 252 and be substantially straight from the distal end 244 to the handle portion 248 forming an angle at the junction of the handle portion 248 and the portion of the instrument 240 that engages the connecting element 18 and flexible member 19.

Figure 20:
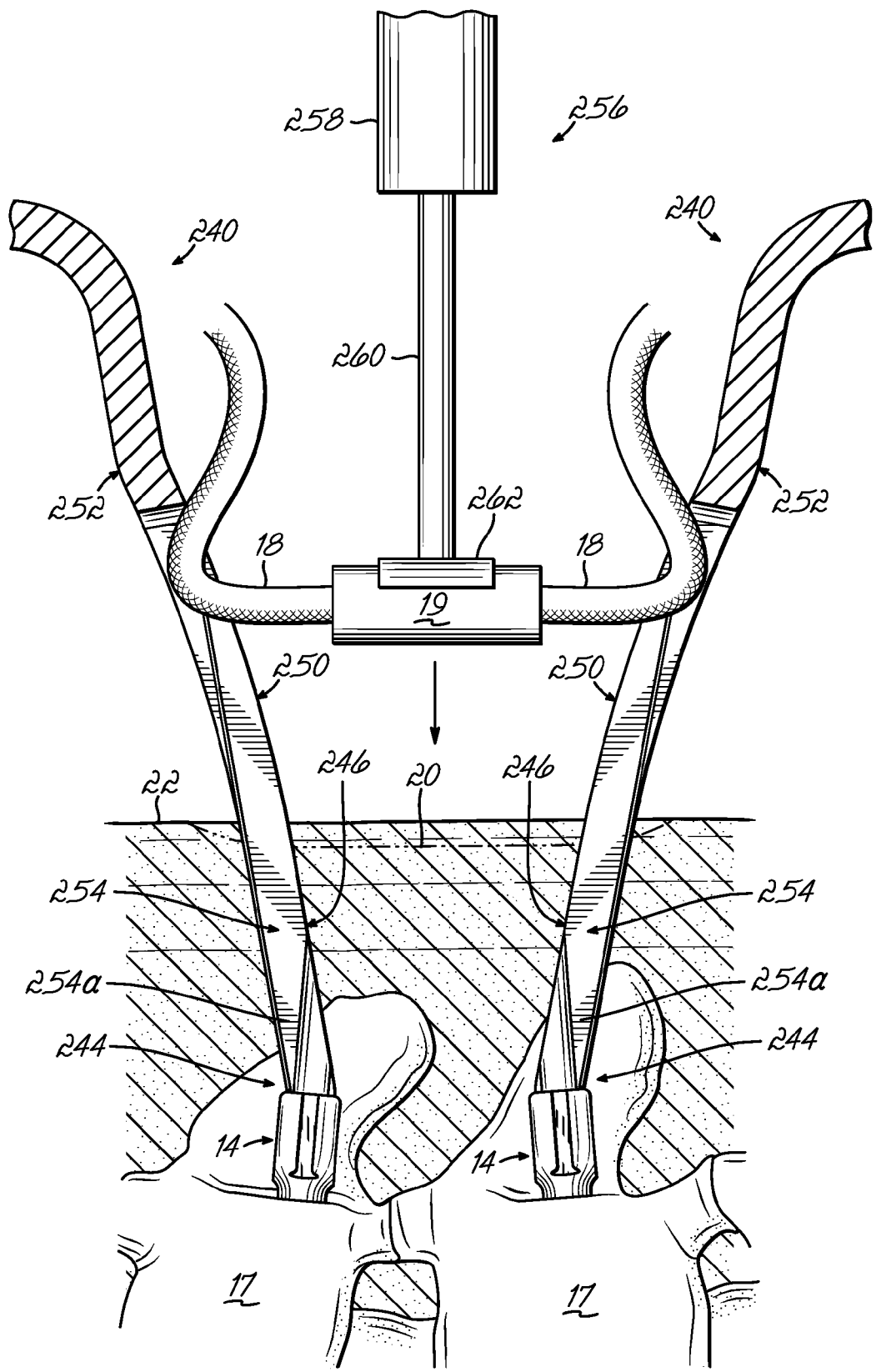
FIG. 20 is a perspective view of FIG. 19 with the flexible member and connecting element being directed along the instruments of FIGS. 18A-C toward the anchors with the aid of a pushing instrument.

Referring now to FIG. 20, the surgeon continues to move the connecting element 18 and flexible member 19 construct toward the spine of the patient. The surgeon may use a pushing instrument 256 to aid in movement of the connecting element 18 and flexible member 19 construct. The pushing instrument 256 may include a handle portion 258, a shaft 260 and a mating portion 262 that engages the flexible member 19. Alternatively, the pushing instrument 256 can include a mating portion that engages the connecting element or both the connecting element and the flexible member. The connecting element 18 can be passed into the guiding slot 254 during the movement of the flexible construct toward the spine. The surgeon can either use the instruments 240 to create distraction between the vertebrae. Alternatively, the flexible element 19 may create the distraction between the vertebrae as the flexible element 19 moves the instruments 240 apart as the flexible element 19 moves toward the spine.

Figure 21:
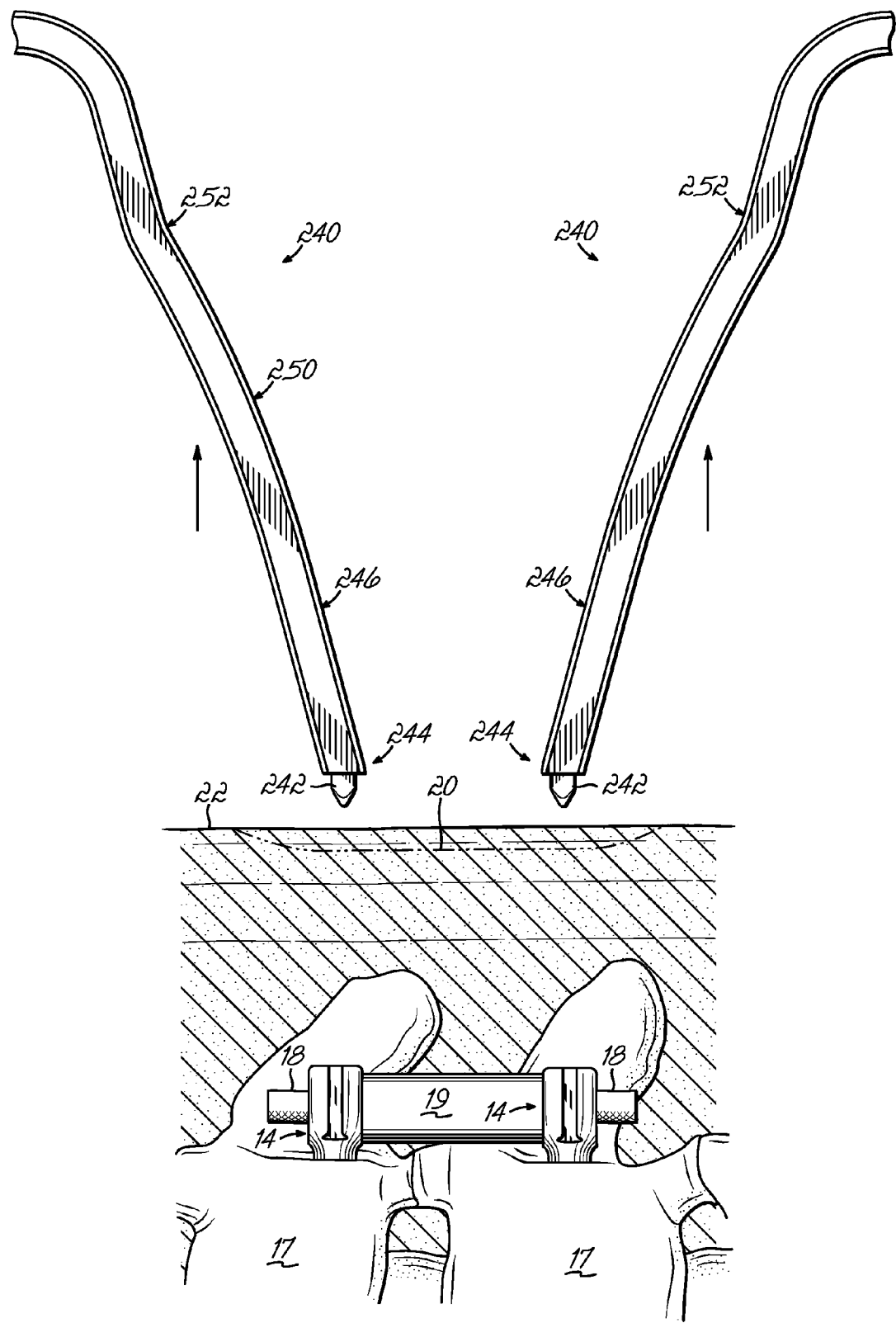
FIG. 21 illustrates the apparatus of FIG. 19 with the flexible member installed between the anchors and the instruments of FIGS. 18A-C being removed from the surgical site.

Referring now to FIG. 21, the flexible member 19 is shown in position between the vertebral anchors 14 and the connecting element 18 is located within the vertebral anchors 14. Following release of the instruments 240 from the vertebrae, a securing member (not shown), such as set screw, may be engaged by a driver or other installation tool suitable to secure the connecting member 18 to the vertebral anchors. For example, the instruments shown in FIGS. 1-17 may be used to guide securing member into engagement with threads on the vertebral anchors 14. Following placement of the securing member, the outer ends of the connecting element 18 may be trimmed and the incision 20 closed to complete the installation.

Persons of ordinary skill in the art will readily appreciate that any one or more of the features described above with regard to any of the exemplary embodiments of FIGS. 1-21 may be combined with any other features and/or embodiments shown therein.

From the above disclosure of the general principles of this invention and the preceding detailed description of at least one embodiment, those skilled in the art will readily comprehend the various modifications to which this invention is susceptible. Therefore, it is intended for the invention to be limited only by the scope of the following claims and equivalents thereof.

We claim:

1. A system for implantation of a spinal stabilization system comprising:
 a vertebral anchor adapted to receive a connecting element and having a threaded shaft adapted to be screwed into a vertebrae, the threaded shaft having a central longitudinal axis, the vertebral anchor including a top portion defining a channel extending therethrough, the top portion having a perimeter and a first engaging element; and
 an installation tool having an elongate shaft and a handle extending at an angle from the elongate shaft, the installation tool including a second engaging element extending from a distal end surface of a straight distal portion of the elongate shaft which is configured to engage with said first engaging element, the second engaging element extending along a first longitudinal axis and the straight distal portion of the elongate shaft extending along a second longitudinal axis non-parallel to the first longitudinal axis;

wherein the elongate shaft includes an elongate slot aligned with the second longitudinal axis which extends from the distal end surface of the elongate shaft through the straight distal portion of the elongate shaft to a location proximate the handle, the elongate slot having a length sufficient to extend exterior of a patient when the installation tool is coupled to the vertebral anchor, the elongate slot being in communication with the channel of the top portion of the vertebral anchor when the second engaging element is engaged with the first engaging element;

wherein said first engaging element is configured to slidably receive said second engaging element in a direction along said first longitudinal axis; and wherein the first longitudinal axis is parallel to the central longitudinal axis of the threaded shaft and the second longitudinal axis is non-parallel to the central longitudinal axis of the threaded shaft.

2. The system of claim 1 wherein said first engaging element is further configured as a female element.

3. The system of claim 2 wherein said female element further comprises a generally trapezoidal shape.

4. The system of claim 1 wherein said second engaging element is further configured as a male element.

5. The system of claim 4 wherein said male element further comprises a generally trapezoidal shape.

6. The system of claim 1 wherein said slot is adapted to guide a connecting element of the spinal stabilization system into said channel of said top portion of said vertebral anchor.

7. The system of claim 6 further comprising:
a securing member configured to secure the connecting element of the spinal stabilization system in said channel of said top portion of said vertebral anchor.

8. The system of claim 1 wherein said second engaging element is fully confined within said perimeter of said top portion.

9. The system of claim 1 wherein said second engaging element further comprises a tapered end adapted to facilitate engagement thereof with said first engaging element.

10. The system of claim 1 wherein said distal end surface is at an oblique angle to the second longitudinal axis.

11. The system of claim 10 wherein said distal end surface abuts a top end surface of the top portion of the vertebral anchor when the installation tool is engaged therewith.

12. A system for implantation of a spinal stabilization system including a connecting element to restrict relative movement of two adjacent vertebrae, the system comprising:
a pedicle screw having a threaded shaft adapted to be screwed into one of the vertebrae, the threaded shaft having a central longitudinal axis, the pedicle screw including a top portion having a channel adapted to receive the connecting element therein, a perimeter, and a pair of first engaging elements extending parallel to the central longitudinal axis of the threaded shaft; and
an installation tool having an elongate shaft and a handle extending at an angle from the elongate shaft, the elongate shaft having a length from the handle to a distal end of the elongate shaft, the elongate shaft defined by a first elongate leg and a second elongate leg spaced from the first elongate leg by an elongate slot, said elongate slot extending a majority of the length of the elongate shaft, the installation tool further including a pair of second engaging elements extending from the distal end of the elongate shaft at an oblique angle to a longitudinal axis of the elongate shaft, said second engaging elements configured to cooperate with said pair of first engaging elements, said slot configured to guide the connecting element toward the channel of said top portion of said pedicle screw;
wherein each of said first engaging elements is configured to slidably receive one of said second engaging elements therein in a direction parallel to the central longitudinal axis of the threaded shaft.

13. The system of claim 12 wherein said first engaging elements are further configured as a trapezoidal-shaped female elements.

14. The system of claim 13 wherein said second engaging elements are further configured as a trapezoidal-shaped male elements.

15. The system of claim 12 wherein the elongate shaft includes a straight distal end portion extending along the longitudinal axis of the elongate shaft to the distal end of the elongate shaft.

16. The system of claim 12 further comprising:
a securing member configured to secure the connecting element of the spinal stabilization system in said channel of said top portion of said pedicle screw.

17. The system of claim 12 wherein said channel is a generally U-shaped channel generally aligned with the slot of the installation tool when said second engaging elements are slidably received in said first engaging elements.

18. A system for implantation of a spinal stabilization system comprising:
a pedicle screw adapted to receive a connecting element, the pedicle screw having a head portion and a threaded shaft extending from the head portion, the threaded shaft having a central longitudinal axis, the head portion including a first elongate slot on a first side of the head portion and a second elongate slot on a second side of the head portion opposite the first side, the first and second elongate slots extending parallel to the central longitudinal axis of the threaded shaft; and
an installation tool including an elongate shaft and a handle extending at an angle from the elongate shaft, the elongate shaft having a length measured from the handle to a distal end of the elongate shaft, the elongate shaft including a first leg and a second leg spaced from the second leg to define an elongate channel between the first leg and the second leg, the elongate channel extending a majority of the length of the elongate shaft, a first protrusion extending distally from a distal end of the first leg and a second protrusion extending distally from a distal end of the second leg parallel to the first protrusion, the first and second protrusions extending at an oblique angle to the first and second legs;
wherein the first and second elongate slots of the head portion of the pedicle screw are configured to slidably receive the first and second protrusions of the installation tool.

19. The system of claim 18, wherein the head portion of the pedicle screw includes a generally U-shaped channel, wherein the elongate channel of the installation tool is generally aligned with the generally U-shaped channel when the installation tool is engaged with the head portion of the pedicle screw.

20. The system of claim 19, wherein the head portion has a longitudinal axis perpendicular to a longitudinal axis of the generally U-shaped channel, wherein the elongate shaft of the installation tool is non-parallel to the longitudinal axis of the head portion when the installation tool is engaged with the head portion of the pedicle screw.

21. A system for implantation of a spinal stabilization system comprising:

a first pedicle screw configured to be secured to a first vertebra of a spinal column, the first pedicle screw including a top portion defining a U-shaped channel and a threaded shaft extending from the top portion of the first pedicle screw to a distal end of the threaded shaft of the first pedicle screw;

a second pedicle screw configured to be secured to a second vertebra of a spinal column, the second pedicle screw including a top portion defining a U-shaped channel and a threaded shaft extending from the top portion of the second pedicle screw to a distal end of the threaded shaft of the second pedicle screw;

wherein the threaded shaft of the first pedicle screw has a central longitudinal axis and the threaded shaft of the second pedicle screw has a central longitudinal axis, the central longitudinal axis of the threaded shaft of the first pedicle screw converging toward the central longitudinal axis of the threaded shaft of the second pedicle screw in a direction toward the top portion of the first pedicle screw from the distal end of the threaded shaft of the first pedicle screw;

a first installation tool including an elongate shaft and a handle extending at an angle from the elongate shaft, the elongate shaft having a length measured from the handle to a distal end of the elongate shaft and a longitudinal axis, the elongate shaft including an elongate channel extending a majority of the length of the elongate shaft, the first installation tool engaged with the top portion of the first pedicle screw such that the elongate channel is in communication with the U-shaped channel of the top portion of the first pedicle screw; and a second installation tool including an elongate shaft and a handle extending at an angle from the elongate shaft, the elongate shaft having a length measured from the handle to a distal end of the elongate shaft and a longitudinal axis, the elongate shaft including an elongate channel extending a majority of the length of the elongate shaft, the second installation tool engaged with the top portion of the second pedicle screw such that the elongate channel is in communication with the U-shaped channel of the top portion of the second pedicle screw;

wherein the longitudinal axis of the first installation tool is non-parallel to the central longitudinal axis of the threaded shaft of the first pedicle screw.

22. The system of claim 21, wherein the longitudinal axis of the elongate shaft of the first installation tool diverges from the longitudinal axis of the elongate shaft of the second installation tool in a direction away from the first pedicle screw.

23. The system of claim 21, wherein the longitudinal axis of the elongate shaft of the second installation tool is non-parallel to the central longitudinal axis of the threaded shaft of the second pedicle screw.

24. The system of claim 21, wherein the top portion of the first pedicle screw includes a first elongate slot on a first side of the top portion and a second elongate slot on a second side of the top portion opposite the first side, the first and second elongate slots extending parallel to the central longitudinal axis of the threaded shaft of the first pedicle screw.

25. The system of claim 24, wherein the first installation tool includes first and second parallel protrusions extending distally from the elongate shaft of the first installation tool, the first and second protrusions being slidably inserted into the first and second elongate slots of the top portion of the first pedicle screw.

26. The system of claim 25, wherein the first and second protrusions extend parallel to the central longitudinal axis of the threaded shaft of the first pedicle screw.

* * * * *